United States Patent [19]

Haworth et al.

[11] Patent Number: 6,046,195
[45] Date of Patent: Apr. 4, 2000

[54] SPIRO-AZACYCLIC DERIVATIVES, THEIR PREPARATION AND THEIR USE AS TACHYKININ ANTAGONISTS

[75] Inventors: Karen Elizabeth Haworth, Sawbridgeworth; Eileen Mary Seward, Bishops Stortford; Christopher John Swain, Duxford, all of United Kingdom

[73] Assignee: Merck Sharp & Dohme Ltd., Hoddesdon, United Kingdom

[21] Appl. No.: 09/269,249

[22] PCT Filed: Sep. 18, 1997

[86] PCT No.: PCT/GB97/02532

§ 371 Date: Mar. 23, 1999

§ 102(e) Date: Mar. 23, 1999

[87] PCT Pub. No.: WO98/13369

PCT Pub. Date: Apr. 2, 1998

[30] Foreign Application Priority Data

Sep. 25, 1996 [GB] United Kingdom .................... 9619994
May 23, 1997 [GB] United Kingdom .................... 9710745

[51] Int. Cl.$^7$ .......................... A61K 31/40; A61K 31/445
[52] U.S. Cl. ............................................... 514/242
[58] Field of Search ...................... 514/242–243, 514/252, 256, 269, 272, 274, 343, 359, 362, 363–365, 369–370, 372, 374, 376, 377, 378, 380, 382, 383, 384, 386, 389, 392, 397, 403, 404, 406, 407; 544/182, 194, 209, 212, 238, 301, 311, 316, 406, 407, 408, 409, 336; 546/16, 278.4; 548/127–133, 134, 135, 136, 138, 139, 143, 144, 182–186, 213–214, 226, 228, 229, 233, 235, 243–247, 251–252, 255, 263.2, 263.4, 263.8, 264.2, 264.8, 265.2, 267.2, 314.7

[56] References Cited

U.S. PATENT DOCUMENTS 5,688,806  11/1997  Desai et al. .............................. 514/278

FOREIGN PATENT DOCUMENTS

WO 97/19084  5/1987  WIPO .
WO 94/20500  9/1994  WIPO .

*Primary Examiner*—Richard L. Raymond
*Assistant Examiner*—Sudhaker Patel
*Attorney, Agent, or Firm*—J. Eric Thies; David L. Rose

[57] ABSTRACT

The present invention relates to certain spiro-azacyclic derivatives which are tachykinin antagonists and are useful, for example, in the treatment or prevention of pain, inflammation, migraine, emesis and postherpetic neuralgia.

20 Claims, No Drawings

SPIRO-AZACYCLIC DERIVATIVES, THEIR PREPARATION AND THEIR USE AS TACHYKININ ANTAGONISTS

This invention relates to a class of azacyclic compounds which are useful as tachykinin antagonists. More particularly, the compounds of the invention are spiro-substituted azacyclic derivatives.

International (PCT) patent specification no. WO 94/20500 (published Sep. 15th, 1994) discloses spiroazacyclic derivatives as substance P antagonists. In particular, WO 94/20500 relates to spirocyclic piperidine derivatives containing a 1,8-diazaspiro[5.5]undecane core.

We have now found a further class of non-peptides which are potent antagonists of tachykinins, especially of substance P.

The present invention provides compounds of the formula (I):

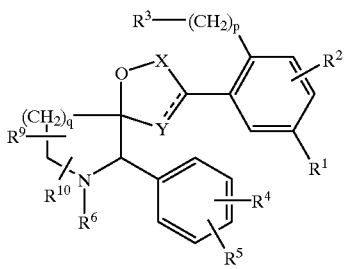

(I)

wherein
$R^1$ represents hydrogen, hydroxy, $C_{1-6}$alkyl, $C_{2-6}$alkenyl, $C_{3-7}$cycloalkyl, $C_{3-7}$cycloalkyl$C_{1-4}$alkyl, fluoro$C_{1-6}$alkyl, $C_{1-6}$alkoxy, fluoro$C_{1-6}$alkoxy, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, benzyloxy, cyano, halogen, $NR^{11}COR^{14}$, $NR^aR^b$, $SR^a$, $SOR^a$, $SO_2R^a$, $OSO_2R^a$, or $C_{1-4}$alkyl substituted by cyano or $CO_2R^a$, where $R^a$ and $R^b$ each independently represent hydrogen, $C_{1-4}$alkyl or fluoro$C_{1-4}$alkyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two oxygen atoms;

$R^3$ represents a 5- or 6-membered aromatic heterocyclic group containing 1, 2, 3 or 4 heteroatoms, selected from nitrogen, oxygen and sulphur, which group is optionally substituted by one or two groups selected from halogen, $C_{1-6}$alkyl, $C_{1-6}$alkoxy, $C_{3-7}$cycloalkyl, $C_{3-7}$cycloalkyl$C_{1-4}$alkyl, trifluoromethyl, trifluoromethoxy, nitro, cyano, $SR^a$, $SOR^a$, $SO_2R^a$, $COR^a$, $CO_2R^a$, phenyl, $-(CH_2)_rNR^aR^b$, $-(CH_2)_rNR^aCOR^b$, $-(CH_2)_rCONR^aR^b$, or $CH_2C(O)R^a$, where $R^a$ and $R^b$ are each independently hydrogen or $C_{1-4}$alkyl and r is zero, 1 or 2;

$R^4$ represents hydrogen, halogen, $C_{1-6}$alkyl, $C_{1-6}$alkoxy, trifluoromethyl, trifluoromethoxy, nitro, cyano, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^5$ represents hydrogen, halogen, $C_{1-6}$alkyl, trifluoromethyl or $C_{1-6}$alkoxy substituted by $C_{1-4}$alkoxy;

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, cyano, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}$alkyl$R^{12}$, $CONR^{13}C_{2-6}$alkenyl, $CONR^{13}C_{2-6}$alkynyl, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl), where $R^a$ and $R^b$ are each independently hydrogen or $C_{1-4}$alkyl;

or $R^6$ represents a group of the formula $-CH_2C\equiv CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula $ZNR^7R^8$ where
Z is $C_{1-6}$alkylene or $C_{3-6}$cycloalkyl;
$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;
$R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom;

$R^9$ and $R^{10}$ each independently represent hydrogen, halogen, $C_{1-6}$alkyl, $CH_2OR^d$, oxo, $CO_2R^a$ or $CONR^aR^b$ where $R^a$ and $R^b$ are each independently hydrogen or $C_{1-6}$alkyl and $R^d$ represents hydrogen, $C_{1-6}$alkyl or phenyl;

$R^{11}$ represents hydrogen, $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^{12}$ represents $OR^a$, $CONR^aR^b$ or heteroaryl, where $R^a$ and $R^b$ are each independently hydrogen or $C_{1-4}$alkyl;

$R^{13}$ represents H or $C_{1-6}$alkyl;

$R^{14}$ represents $C_{1-6}$alkyl, $C_{1-6}$alkoxy, fluoro$C_{1-6}$alkyl or phenyl;

p is zero or 1;
q is 1 or 2; and
X represents $-CH_2-$ or $-CH_2CH_2-$;
Y represents $-CH=$, $-CH_2-$, $-CH_2CH=$ or $-CH_2CH_2-$, with the proviso that the sum total of carbon atoms in X+Y is 2 or 3; and when X is $-CH_2-$ and Y is $-CH=$ or $-CH_2CH=$, the broken line represents a double bond;
and pharmaceutically acceptable salts thereof.

One particular sub-class of compound of formula (I) is that wherein: $R^1$ represents $C_{1-6}$alkyl, $C_{1-6}$alkoxy, fluoro$C_{1-6}$alkyl, fluoro$C_{1-6}$alkoxy, $C_{1-6}$alkoxy$C_{1-4}$alkyl, $C_{1-6}$alkoxy$C_{1-4}$alkoxy, $C_{3-7}$cycloalkyl, $C_{3-7}$cycloalkoxy, $C_{3-7}$cycloalkyl$C_{1-4}$alkyl, $C_{3-7}$cycloalkyl$C_{1-4}$alkoxy, halogen, cyano or $-NR^{11}COCF_3$;
and pharmaceutically acceptable salts thereof.

A particularly preferred class of compound of formula (I) is that wherein $R^1$ is a methyl, trifluoromethyl, methoxy, ethoxy, isopropoxy or trifluoromethoxy group, especially a trifluoromethoxy group.

Another preferred class of compound of formula (I) is that wherein $R^2$ is a hydrogen, fluorine or chlorine atom, especially a hydrogen atom.

A further preferred class of compound of formula (I) is that wherein $R^4$ is a hydrogen atom or a fluorine atom.

Another preferred class of compound of formula (I) is that in which $R^5$ is a hydrogen atom.

Also preferred is the class of compound of formula (I) in which $R^9$ and $R^{10}$ are both hydrogen atoms.

A further preferred class of compound of formula (I) is that wherein $R^6$ is a hydrogen atom.

Also preferred is the class of compound of formula (I) in which $R^6$ is a $C_{1-6}$alkyl group, in particular $CH_2$, $CH(CH_3)$ and $CH_2CH_2$ and especially $CH_2$, substituted by a 5-membered heterocyclic ring containing 2 or 3 nitrogen atoms as previously defined.

In particular, the 5-membered ring is a heterocyclic ring selected from:

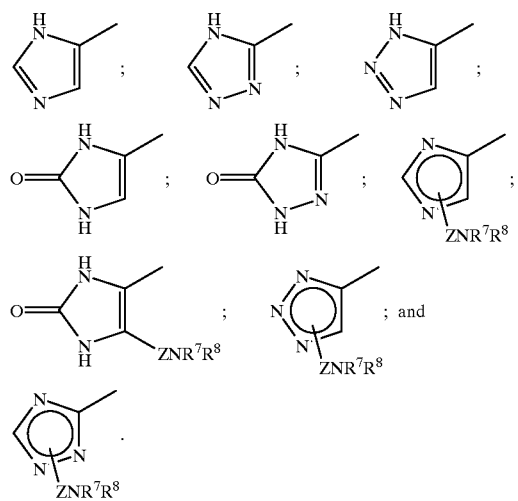

Particularly preferred heterocyclic rings are selected from:

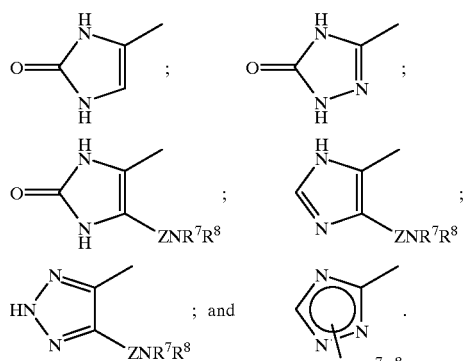

Most especially, the heterocyclic ring is selected from:

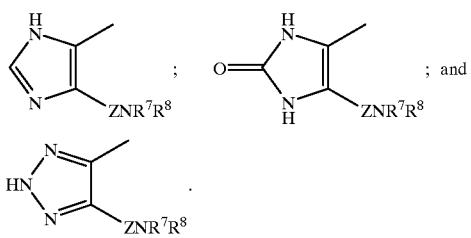

A particularly preferred heterocyclic ring is:

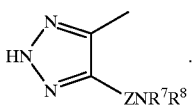

Preferably the double bond represented by the broken line is absent.

Where $R^1$ and $R^2$ are attached to adjacent carbon atoms and are joined together such that there is formed a 5- or 6-membered saturated or unsaturated ring containing one or two oxygen atoms, there is formed a fused ring moiety such as 2,3-dihydrobenzofuran, benzofuran, 3,4-dihydro-2H-1-benzopyran, 2H-1-benzopyran, 1,3-benzodioxole or 1,4-benzodioxan. Particularly preferred is 2,3-dihydrobenzofuran where the oxygen atom corresponds to the position of $R^1$.

Certain particularly apt compounds of the present invention include those wherein $R^3$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each heteroaryl group being optionally substituted as previously defined.

Preferred compounds of the present invention are those wherein $R^3$ is a group selected from furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each heteroaryl group being optionally substituted as previously defined.

Particularly preferred compounds of the present invention are those wherein $R^3$ is a group selected from furan, pyridine, pyrimidine, 1,2,3-triazole, 1,2,4-triazole and tetrazole, each heteroaryl group being optionally substituted as previously defined.

Another preferred class of compounds of the present invention is that wherein $R^3$ is a group selected from tetrazole, furan, thiazole, thiene, pyridine, oxazole, pyrazine and pyrimidine, each heteroaryl group being optionally substituted as previously defined.

A further preferred class of compounds of the present invention is that wherein $R^3$ is a group selected form tetrazole, furan, thiazole, thiene, pyridine, oxazole, pyrazole, pyrimidine and isoxazole, each heteroaryl group being optionally substituted as previously defined.

Preferably, the group $R^3$ is unsubstituted or substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, trifluoromethoxy, nitro, cyano, $SR^a$, $SOR^a$, $SO_2R^a$, $COR^a$, $CO_2R^a$, phenyl, —$(CH_2)_rNR^aR^b$, —$(CH_2)_rNR^aCOR^b$, —$(CH_2)_rCONR^aR^b$ or $CH_2C(O)R^a$ where $R^a$ and $R^b$ are each independently hydrogen or $C_{1-4}$alkyl, and r is zero, 1 or 2.

A particularly preferred class of compound is that wherein the group $R^3$ is unsubstituted or monosubstituted. Particularly preferred substitutents on the group $R^3$ are halogen, $C_{1-6}$alkyl, $C_{1-6}$alkoxy, $CF_3$, $OCF_3$, $NO_2$, $CN$, $SR^a$, $SOR^a$, $SO_2R^a$, $COR^a$, $CO_2R^a$, $-(CH_2)_rCONR^aR^b$, $(CH_2)_rNR^aR^b$, and $(CH_2)_rNR^aCOR^b$ where $R^a$ and $R^b$ are as previously defined. Especially preferred substituents (when present) are $C_{1-4}$alkyl, especially methyl, and trifluoromethyl.

An especially preferred class of compound of formula (I) is that wherein $R^3$ is the group

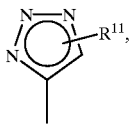

where $R^{11}$ is hydrogen, halogen, $C_{1-6}$alkyl, $C_{1-6}$alkoxy, $CF_3$, $OCF_3$, $NO_2$, $CN$, $SR^a$, $SOR^a$, $SO_2R^a$, $COR^a$, $CO_2R^a$, $(CH_2)_rCONR^aR^b$, $(CH_2)_rNR^aR^b$ or $(CH_2)_rNR^aCOR^b$, where $R^a$ and $R^b$ are hydrogen or $C_{1-4}$alkyl, and r is zero, 1 or 2.

Another especially preferred class of compound of formula (I) is that wherein $R^3$ is the group

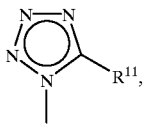

wherein $R^{11}$ is as previously defined.

$R^{11}$ is preferably hydrogen, $C_{1-4}$alkyl, especially methyl, or $CF_3$.

Preferably p is zero.

Preferably q is 2.

Preferably X is $-CH_2-$.

Preferably Y is $-CH_2-$ or $-CH=$.

One favoured group of compounds of the present invention are of the formula (Ia) and pharmaceutically acceptable salts thereof:

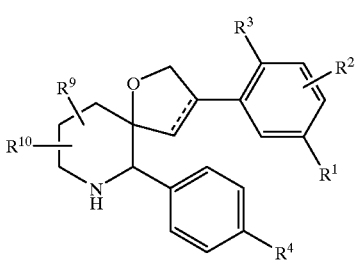

(Ia)

wherein $R^1$, $R^2$, $R^3$, $R^4$, $R^9$, $R^{10}$ and the broken line are as defined in relation to formula (I).

Another favoured group of compounds of the present invention are of the formula (Ib) and pharmaceutically acceptable salts thereof:

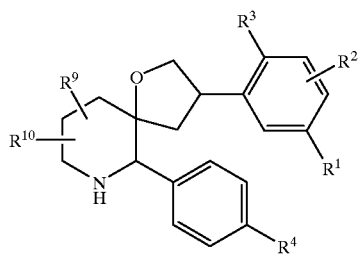

(Ib)

wherein $R^1$, $R^2$, $R^3$, $R^4$, $R^9$ and $R^{10}$ are as defined in relation to formula (I).

With respect to compounds of the formula (I), Z (where present), may be a linear, branched or cyclic group. Favourably Z contains 1 to 4 carbon atoms and most favourably 1 or 2 carbon atoms. A particularly favourable group Z is $CH_2$.

With respect to compounds of the formula (I), $R^7$ may aptly be a $C_{1-4}$alkyl group or a $C_{2-4}$alkyl group substituted by a hydroxyl or $C_{1-2}$alkoxy group, $R^8$ may aptly be a $C_{1-4}$alkyl group or a $C_{2-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazine or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.3.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

In the group $ZNR^7R^8$, Z is preferably $CH_2$ or $CH_2CH_2$, and especially $CH_2$.

The group $NR^7R^8$ preferably represents amino, methylamino, dimethylamino, diethylamino, azetidinyl, pyrrolidino and morpholino.

In particular, $NR^7R^8$ is preferably dimethylamino, azetidinyl or pyrrolidino, especially dimethylamino.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and "fluoro$C_{1-6}$alkoxy" means a $C_{1-6}$alkyl or $C_{1-6}$alkoxy group in which one or more (in particular, 1 to 3) hydrogen atoms have been replaced by fluorine atoms. Similarly the term "fluoroC$_{1-4}$ alkyl" means a C$_{1-4}$alkyl group in which one or more (in particular, 1 to 3) hydrogen atoms have been replaced by fluorine atoms. Particularly preferred are fluoroC$_{1-3}$alkyl and fluoroC$_{1-3}$alkoxy groups, for example, CF$_3$, CH$_2$CH$_2$F, CH$_2$CHF$_2$, CH$_2$CF$_3$, OCF$_3$, OCH$_2$CH$_2$F, OCH$_2$CHF$_2$ or OCH$_2$CF$_3$, and most especially CF$_3$, and OCF$_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "heteroaryl" as a group or part of a group means a 5- or 6-membered heteroaromatic ring containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, and tetrazolyl.

When used herein the term "halogen" means fluorine, chlorine, bromine and iodine. The most apt halogens are fluorine and chlorine of which fluorine is preferred, unless otherwise stated.

Specific compounds within the scope of this invention include:
(6S,5R)-3-(5-methoxy-2-(5-trifluoromethyl)tetrazol-1-yl) phenyl)-6-phenyl-1-oxa-7-aza-spiro[4.5]dec-3-ene;
(6S,5R,3S)-3-(5-methoxy-2-(5-trifluoromethyl)tetrazol-1-yl)phenyl)-6-phenyl-1-oxa-7-aza-spiro[4.5]decane;
(6S,5R)-3-(5-methoxy-2-(tetrazol-1-yl)phenyl)-6-phenyl-1-oxa-7-aza-spiro[4.5]dec-3-ene;
(6S,5R,3S)-3-(5-methoxy-2-(tetrazol-1-yl)phenyl)-6-phenyl-1-oxa-7-aza-spiro[4.5]decane;;
and pharmaceutically acceptable salts thereof.

Further preferred compounds within the scope of this invention include:
(5R,6S)-3-(2-(fur-2-yl)-5-(trifluoromethoxy)phenyl)-6-phenyl-7-aza-1-oxa-spiro[4.5]dec-3-ene;
(3S,5R,6S)-3-(2-(fur-2-yl)-5-(trifluoromethoxy)phenyl)-6-phenyl-7-aza-1-oxa-spiro[4.5]decane;
(3S,5R,6S)-6-phenyl-3-(2-(thiazol-2-yl)-5-(trifluoromethoxy)phenyl)-7-aza-1-oxa-spiro[4.5]decane;
(3S,5R,6S)-6-phenyl-3-(2-(thien-2-yl)-5-(trifluoromethoxy) phenyl)-7-aza-1-oxa-spiro[4.5]decane;
(3R,5R,6S)-3-(2-(fur-3-yl)-5-(trifluoromethoxy)phenyl)-6-phenyl-7-aza-1-oxa-spiro[4.5]decane;
(3R,5R,6S)-6-phenyl-3-(2-(pyrid-2-yl)-5-(trifluoromethoxy)phenyl)-7-aza-1-oxa-spiro[4.5]decane;
(3R,5R,6S)-6-phenyl-3-(2-(pyrid-3-yl)-5-(trifluoromethoxy)phenyl)-7-aza-1-oxa-spiro[4.5]decane;
(3R,5R,6S)-6-phenyl-3-(2-(pyrid-4-yl)-5-(trifluoromethoxy))phenyl-7-aza-1-oxa-spiro[4.5]decane;
(3R,5R,6S)-6-phenyl-3-(2-(oxazol-2-yl)-5-(trifluoromethoxy)phenyl)-7-aza-1-oxa-spiro[4.5]decane;
(3R,5R,6S)-6-phenyl-3-(2-(pyrazin-2-yl)-5-(trifluoromethoxy)phenyl)-7-aza-1-oxa-spiro[4.5]decane;
(3R,5R,6S)-6-phenyl-3-(2-(pyrimidin-2-yl)-5-(trifluoromethoxy)phenyl)-7-aza-1-oxa-spiro[4.5]decane;
(3R,5R,6S)-3-(2-(fur-2-yl)-5-(trifluoromethoxy)phenyl)-6-phenyl-7-aza-1-oxa-spiro[4.5]decane;
and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid. p-toluenesulphonic acid, maleic acid, succinic acid, acetic acid, citric acid. tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The compounds of the formula (I), (Ia) and (Ib) will have the preferred stereochemistry of the 5- and 6-positions that is possessed by the compound of Example 1 (i.e. 5-(R) and 6-(S)). Thus for example as shown in formula (Ic)

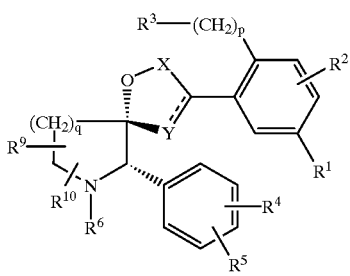

(Ic)

A particularly preferred class of compound of the formula (I), (Ia), (Ib) and (Ic) is that where the double bond represented by the broken line is absent and the stereochemistry of the 3-position is 3-(R).

It will be appreciated that the preferred definitions of the various substituents recited herein may be taken alone or in combination, and apply to the generic formula for compounds of the prsent invention as well as to the preferred classes of compound represented by formulae (Ia), (Ib) and (Ic).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such a corn starch lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as trgacanth, acacia, alginate, dextran, sodium carboxymethylcellulose, methylcellulose polyvinylpyrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsion swill typically contain up to 20% oil, for example, between 5 and 20%. the fat emulsion will preferably comprise fat droplets between 0.1 and 1.0 $\mu$m, particularly 0.1 and 0.5 $\mu$m, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuraligia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis, pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances,* Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubincin, procarbazine, mitomycin, cytarabine, etoposide, methotrexate, 5-fluorouracil, vinblastine, vincristine, bleomycin and chlorambucil [R. J. Gralla et al. in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$antagonist, such as ondansetron, granisetron or tropisetron, or other anti-emetic medicaments, for example, a dopamine antagonist such as metoclopramide or domperidone, or GABA$_B$ receptor agonists such as baclofen. Additionally, a compound of formula (I) either alone or in combination with one or more other anti-emetic therapeutic agents, may be administered in combination with an anti-inflammatory corticosteroid, such as dexamethasone, betamethasone, triamcinolone, triamcinolene acetonide, flunisolide, budesonide, or others such as those disclosed in U.S. Pat. Nos. 2,789,118, 2,99,401, 3,048,581, 3,126,375, 3,929,768, 3,996,359, 3,928,326 and 3,748,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. Pharmacol.,* (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache including migraine, acute or chronic tension headache, cluster headache, temporomandibular pain and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a β$_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D$_4$ antagonist such as a compound selected from those disclosed in European patent specification nos. 0 480 717 and 0 604 114 and in U.S. Pat. No. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and 5-HT$_{1A}$ agonists or antagonists, especially 5-HT$_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-HT$_{1A}$ receptor agonists or antagonists include, in particular, the 5-HT$_{1A}$ receptor partial agonists buspirone, flesinoxan, gepirone an dopsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders.

The present invention also provides a method for the treatment or prevention of eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

In a further embodiment of the present invention there is provided the use of a compound of formula (I) and an anorectic agent for the manufacture of a medicament for the treatment or prevention of obesity.

The present invention also provides a method for the treatment or prevention of obesity, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for the treatment or prevention of bulimia nervosa.

The present invention also provides a method for the treatment or prevention of bulimia nervosa, which method comprises administration to a patient in need of such treatment an amount of a compound of formula (I) and an amount of an anorectic agent, such that together they give effective relief.

In a further embodiment of the present invention there is provided the use of a compound of formula (I) and an anorectic agent for the manufacture of a medicament for the treatment or prevention of compulsive eating disorders.

The present invention also provides a method for the treatment or prevention of compulsive eating disorders, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for reducing the total body fat mass in an obese mammal, especially a human.

The present invention also provides a method for reducing the total body fat mass in an obese mammal, especially a human, which method comprises administration to a patient in need of such treatment an amount of a compound of formula (I) and an amount of an anorectic agent, such that together they give effective relief.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfentluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

Particularly preferred anorectic agents include amphetamine and derivatives thereof such as amphetamine, benzphetamine, chlorphentermine, clobenzorex, cloforex, clotermine, dexfenfluramine, dextroamphetamine, diethylpropion, N-ethylamphetamine, fenfluramine, fenproporex, furfurylmethylamphetamine, levamfetamine, mefenorex, metamfepramone, methamphetamine, norpseudoephedrine, pentorex, phendimetrazine, phenmetrazine, phentermine, phenylpropanolamine, piclorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof;

Particularly preferred halogenated amphetamine derivatives of use in combination with a compound of the present invention include: fenfluramine and dexfenfluramine, and pharmaceutically acceptable salts thereof.

It will be appreciated that for the treatment of prevention of obesity, the compounds of the present invention may also be used in combination with a selective serotonin reuptake inhibitor (SSRI).

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief.

In a further aspect of the present invention, there is provided a pharmaceutical composition for the treatment or prevention of obesity comprising a compound of formula (I) and an SSRI, together with at least one pharmaceutically acceptable carrier or excipient.

It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of formula (I) and an SSRI as a combined preparation for simultaneous, separate or sequential use in the treatment or prevention of obesity.

In an alternative embodiment of the present invention, there is provided the use of a compound of formula (I) and an SSRI for the manufacture of a medicament for reducing the total body fat mass in an obese mammal, especially a human.

The present invention also provides a method for reducing the total body fat mass in an obese mammal, especially a human, which method comprises administration to the mammal an amount of a compound of formula (I) and an amount of an SSRI, such that together they give effective relief.

In a further aspect of the present invention, there is provided a pharmaceutical composition for reducing the total body fat mass in an obese mammal, especially a human, comprising a compound of formula (I) and an SSRI, together with at least one pharmaceutically acceptable carrier or excipient.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared ($kg/m^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrom, Frochlich's syndrom, Type II diabetes, GH-deficient subjects, normal variant short stature, Turner's syndrom, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycycstic ovarian disease, cardiovascular diseases, osteoarthritis, dermatological disorders, hypertension, insulin resistance, hypercholesterolemia, hypertriglyceridemia, and cholelithiasis.

Thus, in one aspect, this invention relates to the inhibition and/or complete suppression of lipogenesis in obese mammals, i.e., the excessive accumulation of lipids in fat cells, which is one of the major features of human and animal obesity, as well as loss of total body weight. In another aspect, the invention ameliorates the conditions that are a consequence of the disease, such as preventing or arresting the progression of polycystic ovarian disease so that the patient is no longer infertile, and increasing the insulin sensitivity and/or decreasing or eliminating the need or usage of insulin in a diabetic patient, e.g., one with adult-onset diabetes or Type II diabetes.

A further aspect of the present invention comprises the use of a compound of formula (I) for achieving a chronobiologic (circadian rhythm phase-shifting) effect and alleviating circadian rhythm disorders in a mammal. The present invention is further directed to the use of a compound of formula (I) for blocking the phase-shifting effects of light in a mammal.

The present invention further relates to the use of a compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of formula (I) or a pharmaceutically acceptable salt thereof.

"Mammals" include animals of economic importance such as bovine, ovine, and procine animals, especially those that produce meat, as well as domestic animals, sports animals, zoo animals, and humans, the latter being preferred.

It will be appreciated that when using any combination described herein, both the compound of formula (I) and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regiment of 1 to 4 times per day, preferably once or twice per day.

In the treatment of emesis using an injectable formulation, a suitable dosage level is about 0.001 to 10 mkg/kg per day, preferably about 0.005 to 5 mg/kg per day, and especially 0.01 to 1 mg/kg per day. The compounds may be administered on a regiment of 1 to 4 times per day, preferably once or twice per day.

It will be appreciated that the amount of a compound of formula (I) required for use in any treatment will vary not only with the particular compounds or composition selected but also with the route of administration, the mature of the condition being treated, and the age and condition of the patient, and will ultimately be at the discretion of the attendant physician.

According to a general process (A.1), the compounds according to the invention in which X is —$CH_2$— and Y is —$CH_2$— or —$CH_2CH_2$— may be prepared by the reduction of a compound of formula (I) in which the broken line represents a double bond, herein after referred to as a compound of formula (IIA)

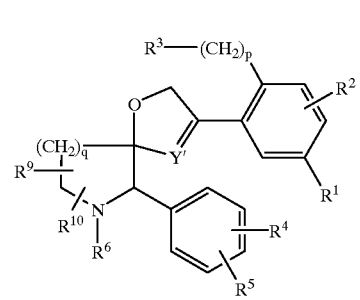

(IIA)

wherein $R^1$, $R^2$, $R^3$, $R^4$, $R^5$, $R^6$, $R^9$, $R^{10}$, p and q are as defined in relation to formula (I) and Y' is —CH= or —$CH_2CH$=.

Suitable reducing conditions include: catalytic hydrogenation using a metal catalyst such as palladium or platinum or hydroxides or oxides thereof, preferably in a suitable solvent such as alcohol, e.g. methanol or ethanol, or an ester, e.g. ethyl acetate, or an organic acid e.g. acetic acid, or a mixture thereof; or using trifluoroacetic acid and triethylsilane.

Similarly, according to a general process (A.2), compounds of formula (I) wherein X is —$CH_2$— and Y is —$CH_2$— or —$CH_2CH_2$—, may be prepared by the reduction of a compound of formula (IIB)

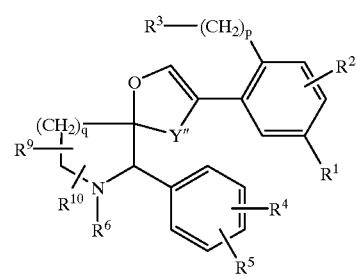

(IIB)

wherein Y" is —$CH_2$— or —$CH_2CH_2$—, using the reaction conditions described in process (A.1), above.

According to another general process (B), compounds of formula (I), in which X is —$CH_2$— and Y is —CH= or —$CH_2CH$= and the broken line is a double bond (i.e.

compounds of formula (II)), may be prepared by the reaction of a compound of formula (III)

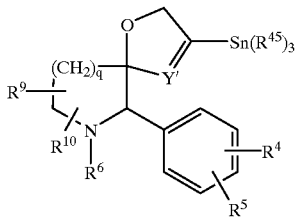
(III)

wherein $R^4$, $R^5$, $R^6$, $R^9$, $R^{10}$ and q are as defined in formula (I), Y' is —CH= or —CH$_2$CH= and each $R^{45}$ is a $C_{1-4}$alkyl group, preferably methyl or butyl groups, with a compound of formula (IV)

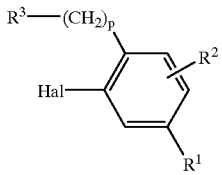
(IV)

wherein $R^1$, $R^2$, $R^3$ and p are as defined in formula (I) and Hal is a halogen atom, for example, chlorine, bromine or iodine, especially bromine.

The reaction is conveniently effected in the presence of lithium chloride and a transition metal catalyst such as tetrakis(triphenylphosphine) palladium (0). Suitable solvents for the reaction include aromatic hydrocarbons, for example, toluene, the reaction being effected at a temperature between 80° C. and the reflux temperature of the solvent.

According to another general process (C), compounds of formula (I) may be prepared by the interconversion of a corresponding compound of formula (I) in which $R^6$ is H, hereinafter referred to as a compound of formula (V)

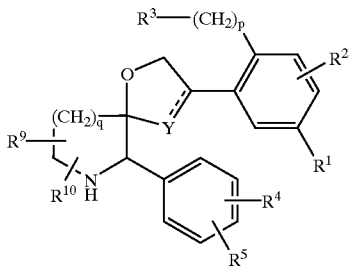
(V)

wherein $R^1$, $R^2$, $R^3$, $R^4$, $R^5$, $R^9$, $R^{10}$, X, Y, p, q and the broken line are as defined in relation to formula (I) by reaction with a compound of formula (VI):

LG—$R^{6a}$ (VI)

where $R^{6a}$ is a group of the formula $R^6$ as defined in relation to formula (I) or a precursor therefor and LG is a leaving group such as a alkyl- or arylsulphonyloxy group (e.g. mesylate or tosylate) or a halogen atom (e.g. bromine, chlorine or iodine); and, $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

According to a further process (D), compounds of formula (I) may be prepared by further interconversion processes from other compounds of formula (I) using suitable procedures. In particular, processes may be used to vary the group $R^6$. For example, compounds of formula (I) wherein $R^6$ is other than H may be prepared from the corresponding compounds of formula (I) wherein $R^6$ is H by reaction with a reagent suitable to introduce the group $R^6$, for example, compounds of formula (I) wherein $R^6$ is COR$^a$ may be prepared form compounds of formula (I) wherein $R^6$ is H by, for example, reaction with an appropriate acid anhydride.

Compounds of formula (I) wherein $R^6$ is $C_{1-6}$alkyl may be prepared from corresponding compounds of formula (I) wherein $R^6$ is COR$^a$ by reduction using, for example, borane or a borohydride such as sodium cyanoborohydride.

Compounds of formula (I) wherein $R^6$ is $C_{1-6}$alkyl substituted by CONR$^a$R$^b$ may be prepared from corresponding compounds of formula (I) wherein $R^6$ is $C_{1-6}$alkyl substituted by CO$_2$R$^a$ by treatment with ammonia or an amine of formula NR$^a$R$^b$.

According to another general process (E), compounds of formula (I) wherein p is zero and $R^3$ is a tetrazol-1-yl group may be prepared by reaction of intermediates of formula (VII)

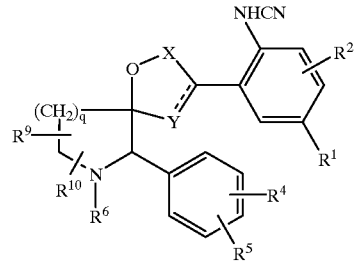
(VII)

with ammonium chloride and sodium azide at elevated temperature, conveniently in a solvent such as dimethylformamide.

According to another general process (F), compounds of formula (I) may be prepared by a coupling reaction between a compound of formula (VIII) and (IX)

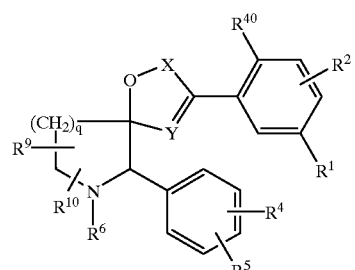
(VIII)

$R^3$—(CH$_2$)$_p$—$R^{41}$ (IX)

wherein one of $R^{40}$ and $R^{41}$ is B(OH)$_2$ or Sn(alkyl)$_3$ or a derivative thereof, and the other is a leaving group such as a halogen atom e.g. bromine or iodine, or —OSO$_2$CF$_3$.

Where one of $R^{40}$ and $R^{41}$ is $B(OH)_2$, the reaction is conveniently effected in the presence of a palladium (0) catalyst such as tetrakis(triphenylphosphine)palladium (0) in a suitable solvent such as an ether, for example, dimethoxyethane at an elevated temperature. Where one of $R^{40}$ and $R^{41}$ is $Sn(alkyl)_3$, the reaction is conveniently effected in the presence of palladium (II) catalyst such as bis(triphenylphosphine) palladium (II) chloride, in a suitable solvent such as an aromatic hydrocarbon, for example, toluene, at an elevated temperature.

According to another general process (G), compounds of formula (I) may be prepared from a compound of formula (X)

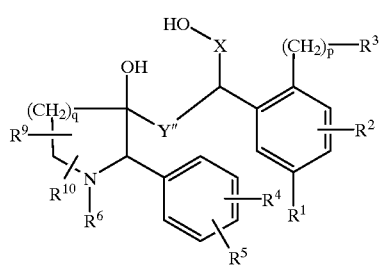

(X)

wherein Y" is —$CH_2$— or —$CH_2CH_2$—, by an acid catalysed intramolecular cyclisation reaction.

Suitable acids of use in the reaction include mineral acids such as hydrochloric acid. The reaction is conveniently effected in a suitable organic solvent, such as an alcohol, e.g. methanol, at an elevated temperature, for example, at the reflux temperature of the chosen solvent.

According to another general process (H), compounds of formula (I) in which X is —$CH_2$— and Y is —$CH_2$— or —$CH_2CH_2$—, may be prepared form a compound of formula (XX)

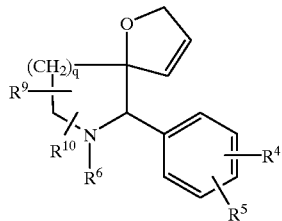

(XX)

by reaction with a compound of formula (IV) wherein Hal in formula (IV) is chlorine, bromine or, preferably, iodine, under the conditions of a reductive Heck reaction using a palladium catalyst such as palladium acetate with, for example, tri-o-tolyphosphine, dimethylformamide and tributylamine, and a reducing agent, preferably formic acid or a salt thereof, such as potassium formate.

According to another general process (J), compounds of formula (I) in which X is —$CH_2$— and Y is —CH= or —$CH_2$CH= (i.e. a compound of formula (IIA), above) may be prepared by the dehydration of a compound of formula (XXI)

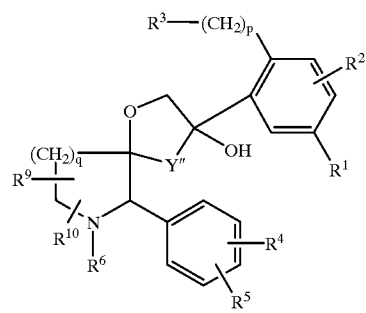

(XXI)

wherein Y" represents —$CH_2$— or —$CH_2CH_2$—, using an acid such as trifluoroacetic acid. The reaction is conveniently effected at a temperature between 0° C. and room temperature, using a suitable organic solvent such as dichloromethane.

Further details of suitable procedures will be found in the accompanying Examples.

Compounds of formula (IIB) may be prepared using the method of general process (J) described above.

Intermediates of formula (V) may be prepared in a similar manner to the methods of processes (A), (B), (E), (F),(G), (H) and (J), preferably with an amino protecting group on the piperdine nitrogen atom. Suitable amino protecting groups include alkoxycarbonyl groups such as tert-butoxycarbonyl and trichloroethoxycarbonyl, aralkyloxycarbnyl groups such as benzyloxycaronyl, or aralkyl groups such as benzyl. Removal of the protecting group is effected by conventional procedures thus, for example, tert-butoxycarbonyl groups may be removed under acidic conditions using, for example, trifluoroacetic acid; tert-butoxycarbonyl groups, together with benzyloxycarobnyl and benzyl groups, may also be removed be hydrogenolysis in the presence of a catalyst, for example, palladium; and trichloroethoxycarbonyl groups may be removed with zinc dust.

Intermediates of formula (III) may be prepared from a compound of formula (XI)

(XI)

wherein $R^{50}$ is a triflate (—$OSO_2CF_3$) group or a bromine or iodine atom, by reaction with a compound of the formula $(R^{45})_3Sn—Sn(R^{45})_3$, for example, hexamethyl distannane. The reaction is conveniently effected in the presence of a base, for example, lethium carbonate, and a catalyst such as triphenylphosphine palladium(0). Suitable solvents for the reaction include ethers such as tetrahydrofuran, the reaction being effected at a temperature between room temperature and 100° C., for example, at about 60° C.

Compounds of formula (XI) may be prepared from a compound of formula (XII):

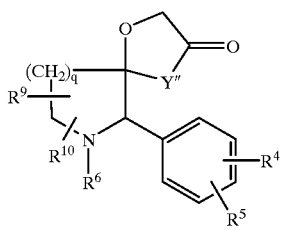

(XII)

by enolisation of the ketone in the presence of a base, for example, sodium hexamethyldisilazide, followed by reaction with a reagent capable of introducing a suitable leaving group, for instance, where $R^{50}$ is —$OSO_2CF_3$, using 2-[N,N-bis(trifluoromethylsulphonyl)amino]-5-chloropyridine or triflic anhydride. The reaction is conveniently effected in a suitable solvent such as an ether, for example, tetrahydrofuran at a reduced temperature, for instance, −80° C.

Compounds of formula (XII) may be prepared from a compound of formula (XIII) by the following reaction sequences (Scheme A or Scheme B) or by methods analogous thereto (with the proviso that $R^9$ and $R^{10}$ are not oxo):

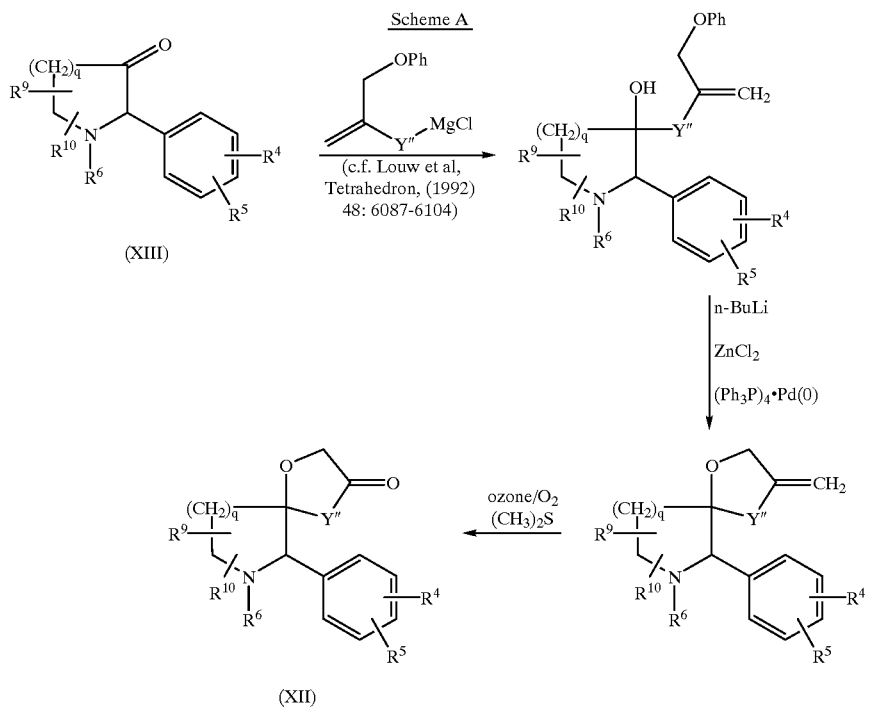

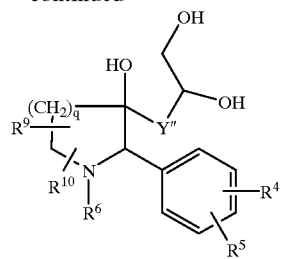
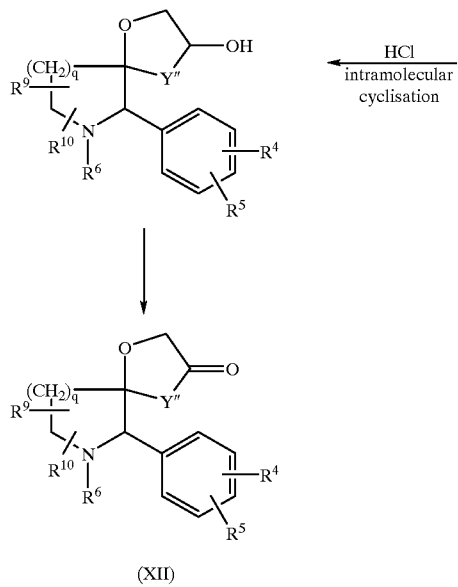

(XII)

In a preferred embodiment of the aforementioned processes, $R^6$ is replaced with an amino protecting group, in particular tert-butoxycarbonyl which is conveniently removed prior to reduction of the 7-aza-spiro[4.5]dec-3-ene structure (general process (A)).

Compounds of formula (III), wherein Y' is —CH=, may also be prepared from a compound of formula (XIII) by the following reaction sequence (Scheme C) or by methods analogous thereto:

Scheme C

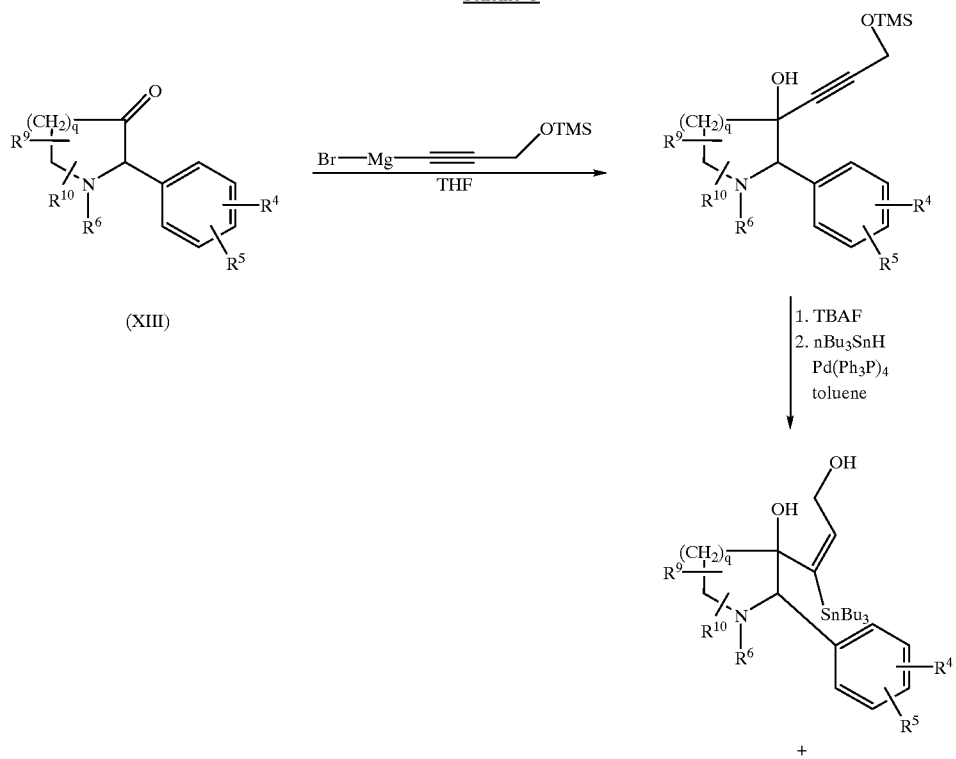

-continued

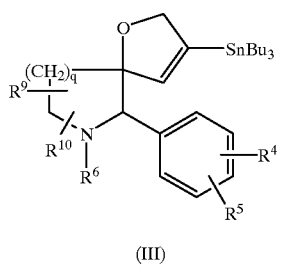

(III)

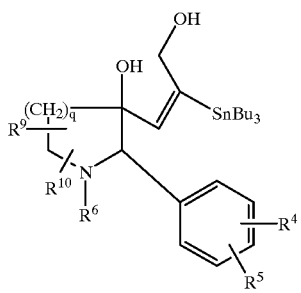

DEAD, Ph₃P, THF

In another preferred embodiment of the aforementioned processes, R⁶ is a benzyl group. The reduction reaction described as process (A) above for the preparation of compounds of formula (I) may conveniently replace the benzyl group with a hydrogen atom (i.e. forming a compound of formula (V)).

Compounds of formula (IV) in which p is zero may be prepared by conventional methodology, for example, from a compound of formula (XIV)

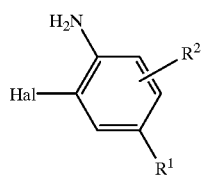

(XIV)

by reaction with a suitable anhydride of the formula $(RCO)_2O$, where R is the desired substituent for the tetrazole 5-position, followed by reaction with triphenylphosphine in carbon tetrachloride, followed by the further step of (i) reaction with an azide such as sodium azide to effect the formation of the tetrazole ring; or (ii) reaction with hydrazine hydrate to effect the formation of a 1,2,4-triazole ring; or (iii) reaction with aminoacetaldehyde diethyl acetal to effect the formation of an imidazolyl ring.

Compounds of formula (XIV) may be prepared from the corresponding nitro compound by reduction using, for example, iron powder, or Raney nickel in a conventional manner.

The compounds of formula (XIV) or their nitro precursors are either known compounds or may be prepared using conventional methodology.

Compounds of formula (VII) may be prepared by reaction of a compound of formula (III) with a compound of formula (XV)

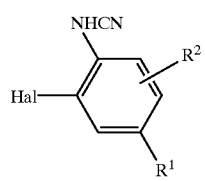

(XV)

according to the methods described above, followed by reduction according to the method of general process (B).

Intermediates of formula (X) wherein Y" is $—CH_2CH_2—$ may be prepared by the reduction of a compound of formula (XVI)

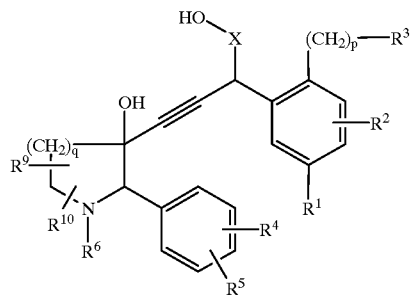

(XVI)

or a protected derivative thereof, using conventional methodology, for instance, by catalytic hydrogenation using a metal catalyst such as palladium or platinum or oxides thereof, preferably in a solvent such as an alcohol, e.g. ethanol, or an ester, e.g. ethyl acetate.

Compounds of formula (XVI) may be prepared by the reaction of a compound of formula (XIII) with a compound of formulae (XVII)

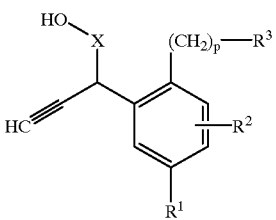

(XVII)

or a protected derivative thereof, by lithiation using n-butyl lithium followed by quenching with, for example, sodium dihydrogen orthophosphate. The reaction is conveniently effected in a solvent such as an ether, e.g. tetrahydrofuran, at a reduced temeprature, for example, at −78° C.

Alternatively, compounds of formula (X) may be prepared by the reaction of a compound of formula (XIII) with a Grignard reagent of formula (XXII)

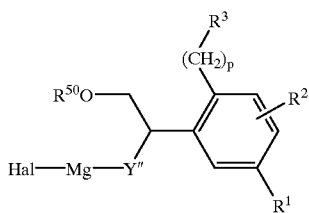

(XXII)

wherein $R^{50}$ is a suitable hydroxy protecting group, preferably benzyl, and Hal is a halogen atom, preferably chlorine, followed by removal of the protecting group $R^{50}$. Utilisation of a chiral intermediate of formula (XXII) is particularly suitable for controlling the stereochemistry of the 3-position in compounds of formula (I).

Compounds of formula (XXII) may be prepared by conventional methods well known in the art.

In a further alternative method, compounds of formula (X) may be prepared by the reduction of a compound of formula (XXIII)

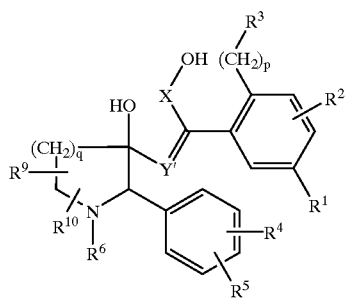

(XXIII)

using, for example, catalytic hydrogenation in the presence of a metal catalyst such as palladium or platinum or hydroxides or oxides thereof, pregerably in a suitable solvent such as an alcohol, e.g. methanol, an ester, e.g. ethyl acetate, or an organic acid, e.g. acetic acid, or a mixture thereof.

Compounds of formula (XXIII) in which Y' is —CH=, may be prepared from a compound of formula (XXIV)

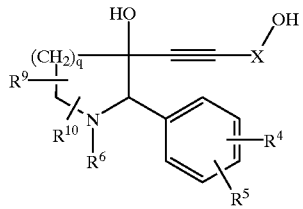

(XXIV)

by reaction with a compound of formula (IV) using reductive Heck conditions as described in general process (H), above.

Compounds of formula (XXIV) may be prepared from compounds of formula (XIII) and, for example, a Grignard reagent prepared from O-trimethylsilylpropargyl alcohol using conventional methodology, followed by removal of the hydroxy protecting group.

According to another method, compounds of formula (X) in which X is —CH$_2$—, may be prepared from a compound of formula (XXV)

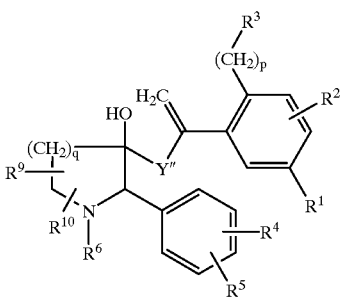

(XXV)

by reaction with borane in tetrahydrofuran, followed by an oxidative work-up using, for example, hydrogen peroxide and sodium hydroxide.

Compounds of formula (XXV) may be prepared from a compound of formula (XIII) and, for example, a Grignard reagent prepared from a 2-aryl-3-bromo-1-propene using conventional methodology.

Compounds of formula (XXI) may be prepared by the reaction of a compound of formula (XII) with Grignard reagent prepared from a compound of formula (IV), preferably using magnesium and a bromide of formula (IV). The coupling reaction is conveniently effected at reduced temperature, for example at about 0° C., using a suitable solvent such as an ether, for example, diethyl ether.

Compounds of formula (XX) may be prepared, for example, by the conversion of a stannane of formula (III) to the corresponding iodide by treatment with iodine at reduced temperature, for example, at about −78° C., in a suitable solvent such as dichloromethane. The iodine may then be displaced to give the compound of formula (XX) by treatment with, for example, α,α'-azo-isobutyronitrile and tributyltin hydride in a suitable solvent, for example, toluene, at an elevated temperature, for example, at about 100° C.

Alternatively, compounds of formula (XX) may be prepared by the cyclisation of a compound of formula (XXVI)

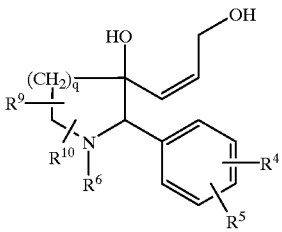

(XXVI)

using the dehydrating conditions described above for general process (J) or using triphenylphosphine and diethylazodicarboxylate in a suitable solvent such as tetrahydrofuran.

Compounds of formula (XXVI) may be prepared by the partial reduction of an acetylene compound of formula (XXIV). The reaction is conveniently effected by catalytic hydrogenation using a metal catalyst such as palladium on calcium carbonate in the presence of a lead poison (e.g. Lindlar catalyst). Other suitable methods will be readily apparent to a person of ordinary skill in the art.

Compounds of formula (XIII) may be prepared by methods described in European Patent Specification No. 0 577 394-A, or by analogous methods.

Compounds of formula (XVII) are known compounds (see Chemische Berichte, (1088) 121, 1315–1320) or may be prepared by methods analogous to those described therein.

Compounds of formula (IX) and (XV) are known compounds or may be prepared by conventional methods or using techniques analogous to those taught herein.

Further useful methodology for the preparation of compounds in which $R^6$ contains a heterocyclic group is described, for example, in International Patent Specification No. WO 95/18124.

It will be appreciated that compounds of the formula (I) wherein $R^6$ contains an =O or =S substituent can exist in tautomeric forms. All such tautomeric forms and mixtures thereof are included within this invention. Most aptly the =O or =S substituent in $R^6$ is the =O substituent.

Where they are not commercially available, the intermediates of formula (VI) above may be prepared by the procedures described in the accompnying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 1 µM on said test method.

For the avoidance of doubt, the nomenclature adhered to throughout this specification follows the general principle illustrated below:

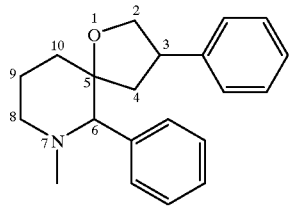

The following non-limiting Examples serve to illustrate the preparation of compounds of the present invention:

DESCRIPTION 1

(2S)-1-tert-Butoxycarbonyl-2-phenylpiperidin-3-one

To a cooled (−60° C.) solution of oxalyl chloride (0.68 ml, 7.8 mmol) in dichloromethane (17 ml) was added dimethyl sulfoxide (0.69 ml, 9.8 mmol) over 10 minutes before addition of (2S,3S)1-tert-butoxycarbonyl-3-hydroxy-2-phenylpiperidine (prepared by the method described in European Patent Specification number 0 528 495-A) in dichloromethane (7 ml). The solution was stirred at −60° C. for 20 minutes, warmed to −30° C. and triethylamine (2.5 ml) added. The solution was warmed to 0° C. then was washed with ice cold 10% aqueous citric acid solution (40 ml, twice) water and dried (MgSO$_4$). The solution was evaporated to dryness to give the title compound and this was used immediately without further purification. $^1$H NMR (250 MHz, CDCl$_3$) δ 7.5–7.3 (5H,m), 5.8 (1H, bs), 4.2 (1H, bs), 3.4 (1H, m), 2.6 (2H, m), 2.0 (2H, m), 1.54 (9H, s).

DESCRIPTION 2

(2S,3R)-1-tert-Butoxycarbonyl-3-hydroxy-3-(2-methylene-3-phenoxypropyl)-2-phenylpiperidine A tetrahydrofuran solution of 3-(chloromagnesio)-2-(phenoxymethyl)-1-propene (0.91 M, 3 ml) (Louw et. al. *Tetrahedron*, 48, 6087–6104, 1992, prepared from 2.74 mmol of 3-chloro-2-(phenoxymethyl)-1-propene) was slowly added to a solution of (2S)-1-tert-butoxycarbonyl-2-phenylpiperidin-3-one (Desc.1) in THF (3 ml). The solution was stirred at room temperature for 1 hour, quenched by addition of saturated ammonium chloride solution (20 ml) and extracted with ethyl acetate (20 ml). The organic phase was washed (saturated brine), dried (MgSO$_4$), evaporated to a small volume and purified by chromatography on silica gel eluting with hexane containing increasing proportions of ethyl acetate between 0% to 20%. Evaporation of the fractions gave (2S,3R)-1-tert-butoxycarbonyl-3-hydroxy-3-(2-methylene-3-phenoxypropyl)-2-phenylpiperidine. MS (ES$^+$) m/z 424 (M+H), 324 (M+2H−$^t$BuOCO—), 368 (M+2H−$^t$Bu). $^1$H NMR (360 MHz, CDCl$_3$) δ 7.48 (2H, d, J 6.9 Hz), 7.35–7.2 (6H, m) 6.9–6.88 (3H, m), 5.4 (1H, s), 5.15 (2H, d, J 13.7 Hz), 4.61 (2H, s), 4.11 (2H, m), 3.17 (1H, m), 2.66 and 2.59 (2H, AB d, J 14.0 Hz), 1.95 (2H, m), 1.79 (2H, m), 1.36 (9H, s).

DESCRIPTION 3

(6S,5R)-3-Methylene-6-phenyl-1-oxa-7-(tert-butoxycarbonyl)aza-spiro[4.5]decane

To a cooled (−80° C.) solution of (2S,3R)1-tert-butoxycarbonyl-3-hydroxy-3-(2-methylene-3-phenoxypropyl)-2-phenylpiperidine (1.53 g, 3.62 mmol; Desc.2) in THF (20 ml) was added a solution n-butyllithium in hexanes (2.5 M, 1.45 ml, 3.62 mmol) followed by a solution of zinc chloride (0.5 M in THF, 7.24 ml, 3.62 mmol). The solution was allowed to warm to room temperature, triphenylphosphine palladium (0) (0.23 g, 0.2 mmol) added, degassed and then heated to reflux for 16 hours. After removal of the solvent by evaporation the residue was partitioned between ethyl acetate and 2 M NaOH. The organic phase was washed with saturated brine, dried (MgSO$_4$) and purified by chromatography on silica gel eluting with hexane containing increasing proportions of ethyl acetate between 0% to 5%. Evaporation of the fractions gave (6S,5R)-3-methylene-6-phenyl-1-oxa-7-(tert-butoxycarbonyl)aza-spiro[4.5]decane. $^1$H NMR (360 MHz, CDCl$_3$) δ 7.58 (2H, d, J 8.4 Hz), 7.32–7.21 (3H, m), 5.23 (1H, s), 5.06 (1H, m), 4.97 (1H, m), 4.39 (2H, AB d, J 13.3 Hz), 3.99 (1H, dd, J 13.3, 4.48 Hz), 2.83 (1H, ABd J 15.5 Hz), 2.7 (1H,td J 12.5 Hz 3.93 Hz) 2.5 (1H, ABd, J 15.4 Hz), 2.15 (2H, td, J 12.3 Hz 4.4 Hz), 1.69 (2H, m), 1.46 (9H, s). MS (ES$^+$) m/z 329 (M+2H−$^t$BuOCO).

DESCRIPTION 4

(6S,5R)-7-(tert-Butoxycarbonyl)-3-keto-6-phenyl-7-aza-1-oxa-spiro[4.5]decane

Through a cooled (−80° C.) solution of (6S,5R)-7-(tert-butoxycarbonyl)-3-methylene-6-phenyl-7-aza-1-oxa-spiro[4.5]decane (0.665 g; Desc.3) in dichloromethane (5 ml) and methanol (5 ml) was bubbled a mixture of ozone and oxygen for 0.75 hours. After the solution had been purged with nitrogen, dimethyl sulphide (0.5 ml) was added and then stirred under nitrogen at room temperature for 16 hours. The solvent was removed in vacuo and the residue partitioned between ethyl acetate and water. The organic phase was dried (MgSO$_4$), evaporated and the residue purified by chromatography on silica gel elutintg with hexane containing increasing proportions of ethyl acetate between 0% to 10%. Evaporation of the fractions gave the title compound. MS (ES$^+$) m/z 332 (M+H), 232 (M+2H-$^t$BuOCO—), 276 (M+2H-$^t$Bu). $^1$H NMR (250 MHz, CDCl$_3$) δ 7.58 (2H, d, J 6.2 Hz), 7.37–7.26 (3H, m), 5.3 (1H, s), 4.15 and 4.09 (2H, AB d, J 17.4 Hz), 3.97 (1H, m), 2.80 (1H, td, J 12.9 Hz and 4.0 Hz), 2.74 and 2.48 (2H, ABd, J 18.1 Hz), 2.29 (2H, m), 1.88–1.63 (2H, m), 1.44 (9H, s).

DESCRIPTION 5

(6S,5R)-7-(tert-Butoxycarbonyl)-3-(trifluoromethylsulfonyloxy)-6-phenyl-7-aza-1-oxa-spiro[4.5]dec-3-ene To a cooled (−80° C.) solution of 1 M sodium hexamethyldisilazide (0.38 ml, 0.38 mmol) in THF was added a solution of (6S,5R)-7-(tert-butoxycarbonyl)-3-keto-6-phenyl-7-aza-1-oxa-spiro[4.5]decane (0.105 mg, 0.319 mmol; Desc.4) in THF (3 ml). The solution was stirred for 1 hour at −80° C. and a solution of 2-[N,N-bis(trifluoromethylsulphonyl)amino]-5-chloropyridine (0.163 g, 0.415 mmol) in THF (3 ml) was added. The solution was stirred at −80° C. for 30 minutes then at room temperature for 30 minutes before being quenched by addition of sat. aq. ammonium chloride solution and ethyl acetate. The dried (MgSO$_4$) organic phase was purified by chromatography on silica gel eluting with hexane containing increasing proportions of ethyl acetate between 0% to 5%. Evaporation of the fractions gave the title compound. MS (ES$^+$) m/z 464 (M+H), 364 (M+2H-$^t$BuOCO—), 408 (M+2H-$^t$Bu). $^1$H NMR (360 MHz, CDCl$_3$) δ 7.4 (2H, d, J 7.3 Hz), 7.3–7.22 (3H, m), 6.01 (1H, t, J 2.13 Hz), 5.13 (1H, s) 4.56 and 4.26 (2H, ABdd, J 12.4 Hz and 1.97 Hz), 4.10 (1H, dt, J 12.6 Hz and 4.22 Hz), 3.00 (1H, m), 2.28–2.04 (2H, m) 1,.88–1.76 (2H, m), 1.37 (9H, s).

DESCRIPTION 6

(6S,5R)-7-(tert-Butoxycarbonyl)-6-phenyl-3-(trimethylstannyl)-7-aza-1-oxa-spiro[4.5]dec-3-ene To a degassed solution of (6S,5R)-7-(tert-butoxycarbonyl)-6-phenyl-3-(trifluoromethylsulphonyloxy)-7-aza-1-oxa-spiro[4.5]dec-3-ene (0.482 g, 1.04 mmol; Desc.5), lithium chloride (0.264 g, 6.25 mmol), lithium carbonate (0.076 g) and hexamethyl distannane (0.96 g, 2.9 mmol) in THF (10 ml) was added triphenylphosphine palladium (0) (0.06 g). The solution was degassed and then heated at 60° C. for 5 hours under nitrogen. Water (20 ml) and ethyl acetate (20 ml) were added and the dried organic phase was purified by chromatography on silica gel (eluting with hexane containing increasing proportions of ethyl acetate between 0% to 5%. Evaporation of the fractions gave the title compound as a crystalline solid. $^1$H NMR (360 MHz, CDCl$_3$) δ 7.25 (2H, d, J 7.3 Hz), 7.1–7.0 (3H, m), 5.83 (1H, t, J 2.5 Hz), 4.78 (1H, s), 4.48 and 4.02 (2H, dd, J 12.9 Hz and 2.3 Hz), 3.96 (1H, dd, J 6.16 Hz and 13.4 Hz), 2.95 (1H, td, J 13.3 Hz and 4.5 Hz), 1.84 (1H, m), 1.68 (1H, m), 1.60 (2H, m), 1.19 (9H, s), 0 (6H, s).

DESCRIPTION 7

3-Bromo-4-(5-(trifluoromethyl)tetrazol-1-yl)anisole
a) 2-Bromo-4-methoxyaniline
To a solution of p-anisidine (10 g, 0.08 mol) and sodium carbonate (17.2 g, 0.16 mol) in dichloromethane (400 ml) was added a solution of bromine (3.8 ml), 0.072 mol) in dichloromethane (200 ml) dropwise. The reaction was stirred at ambient temperature for 45 minutes, diluted with dichloromethane (200 ml) and washed with water (2×200 ml). The organic layer was dried over magnesium sulphate, and the solvent was removed in vacuo to yield a dark brown oil. Chromatography on silica eluting with a gradient of ethyl acetate in hexane (10%, 15% and 20%) afforded the title compound as a dark red oil (4 g, 25%), m/z (ES$^+$) 202 (M$^{30}$ +H, 100%). $^1$H NMR (250 MHz, CDCl$_3$) δ 3.73 (3H, s), 3.78 (2H, broad s), 6.72 (2H, t, J 1.2 Hz), 7.00 (1H, q, J 1.26 Hz).

b) 3-Bromo-4-(trifluoroacetamido)anisole
2-Bromo-4-methoxyaniline (4 g, 0.02 mol) was dissolved in dichloromethane (30 ml) containing triethylamine (2.77 ml, 0.02 mol). The solution was cooled to −10° C. and trifluoroacetic anhydride (2.81 ml, 0.02 mol) was added slowly. The reaction was stirred at ambient temperature for 15 minutes, diluted with dichloromethane (50 ml) and washed with water (2×50 ml). The organic layer was dried over magnesium sulphate and the solvent was removed in vacuo. Chromatography on silica eluting with 10–15% ethyl acetate in hexane afforded the title compound as an orange solid (4.7 g, 79%). $^1$H NMR (360 MHz, CDCl$_3$) δ 3.81 (3H, s), 6.92 (1H, dd, J 2.8 Hz, J 9.1 Hz), 7.15 (1H, d, J 2.8 Hz), 8.14 (1H, d, J 9.1 Hz), 8.23 (1H, broad s).

c) 3-Bromo-4-(5-(trifluoromethyl)tetrazol-1-yl)anisole
3-Bromo-4-(trifluoroacetamido)anisole (4.7 g, 0.16 mol) was suspended in carbon tetrachloride (60 ml) and triphenylphosphine (6.2 g, 0.024 mol) was added. The reaction was heated at reflux for 12 hours. The reaction was allowed to cool to ambient temperature, and filtered. The solid was washed thoroughly with ethyl acetate:diethyl ether (1:1, 200 ml:200 ml). The filtrate was concentrated in vacuo to afford a red solid. This solid was dissolved in N,N-dimethylformamide (10 ml) and this solution was added to sodium azide (1.55 g, 0.024 mol). The reaction was stirred at ambient temperature for 12 hours, and diluted with water (100 ml). The product was extracted into ethyl acetate (3×50 ml) and the combined organics were washed with brine (100 ml), dried over magnesium sulphate and the solvent removed in vacuo. Chromatography on silica eluting with 10% ethyl acetate in hexane afforded the title compound as a pale orange solid (4.2 g, 66%), m/z (ES$^+$) 323 (M$^+$+H, 100%). $^1$H NMR (250 MHz, CDCl$_3$) δ 3.92 (3H, s), 7.03 (1H, dd J 2.7 Hz, J 8.8 Hz), 7.30 (1H, d, J 2.7 Hz), 7.34 (1H, d, J 8.8 Hz).

DESCRIPTION 8

(5R,6S)-7-(tert-butoxycarbonyl)-3-(5-methoxy-2-(5-(trifluoromethyl)-tetrazol-1-yl)phenyl)-6-phenyl-7-aza-1-oxa-spiro[4.5]dec-3-ene A mixture of (5R,6S)-7-(tert-butoxycarbonyl)-6-phenyl-3-(trimethylstannyl)-7-aza-1-oxa-spiro[4.5]dec-3-ene (0.5 g, 1 mmol; Desc.6), lithium chloride (0.266 g, 6 mmol) and 3-bromo-4-(5-(trifluoromethyl)-tetrazol-1-yl)anisole (0.404 g, 1.2 mmol; Desc. 7c) in toluene (15 ml) was degassed and purged with nitrogen before addition of tetrakis (triphenylphosphine)palladium(0) (0.06 g). The mixture was degassed thoroughly, and the solution was heated to 110° C. for 19 hours. The solvent was evaporated in vacuo. The residue was dry loaded onto silica from methanol, and purified by chromatography on silica eluting with 10–20% ethyl acetate in hexane, to afford the title compound as a yellow oil (500 mg, 90%) MS (CI$^+$) m/z 558 (M+H, 60%). $^1$H NMR (250 MHz, CDCl$_3$) δ 1.34 (9H, s), 1.50 (1H, m), 1.55 (1H, m), 1.67 (1H, m), 1.87 (1H, m), 3.08 (1H, m), 3.88 (3H, s), 4.02 (1H, m), 4.30 (1H, dd, J 2.1 Hz, J 12.4 Hz), 4.46 (1H, dd, J 2.1 Hz, J 12.4 Hz), 4.92 (1H, s), 5.30 (1H, t, J 0.9 Hz), 6.68 (1H, d, J 2.8 Hz), 6.98 (1H, dd, J 2.8 Hz, J 8.8 Hz), 7.25 (6H, m).

DESCRIPTION 9

3-Bromo-4-(tetrazol-1-yl)anisole

2-Bromo-4-methoxyaniline (1.2 g, 6 mmol; Desc. 7a) was dissolved in glacial acetic acid (10 ml) and heated to 75° C. To this solution was added triethylorthoformate (2.5 ml, 15 mmol) and heated at 75° C. for 1 hour. Sodium azide (1.16 g, 18 mmol) was added portionwise and reaction heated at 75° C. for a further 3 hours and stirred at ambient temperature for 24 hours. The reaction was diluted with water (100 ml) and product extracted into ethyl acetate (3×70 ml). The combined organics were washed with brine (100 ml), dried over magnesium sulphate and the solvent removed in vacuo. Medium pressure chromatography eluting with 40% ethyl acetate/hexane afforded the title compound as a white solid (1.5 g, 90%). $^1$H NMR (360 MHz, $d_6$-DMSO) δ 3.88 (3H, s), 7.20 (1H, dd, J 2.7 Hz, J 8.8 Hz), 7.51 (1H, d, J 2.7 Hz), 7.68 (1H, d, J 8.8 Hz), 9.83 (1H, s).

DESCRIPTION 10

(5R,6S)-7-(tert-Butoxycarbonyl)-3-(5-methoxy-2-(tetrazol-1-yl)phenyl)-6-phenyl-1-oxa-spiro[4.5]dec-3-ene This compound was prepared according to the procedure described in Description 8. Medium pressure chromatography eluting with 50% ethyl acetate/hexane afforded the title compound as a yellow oil (400 mg, 78%). $^1$H NMR (360 MHz, CDCl$_3$) δ 1.32 (9H, s), 1.67 (3H, m), 1.90 (1H, m), 3.11 (1H, m), 3.88 (3H, s), 4.04 (1H, m), 4.09 (1H, dd, J 2.1 Hz, J 12.4 Hz), 4.40 (1H, dd, J 2.1 Hz, J 12.4 Hz), 4.90 (1H, s), 5.44 (1H, t, J 2.1 Hz), 6.73 (1H, d, J 2.8 Hz), 6.96 (1H, dd, J 2.9 Hz, J 8.8 Hz), 7.25 (5H, m), 7.43 (1H, d, J 8.8 Hz), 8.56 (1H, s).

DESCRIPTION 11

(5R,6S)-3-(2-Benzyloxy-5-(trifluoromethyoxy)phenyl)-7-(tert-butoxycarbonyl)-6-phenyl-7-aza-1-oxa-spiro[4.5]dec-3-ene a) 2-Bromo-4-(trifluoromethyoxy)phenyl To a cooled (0° C.) solution of 4-(trifluoromethoxy)phenol (35.6 g, 0.2 mol) in chloroform (280 ml) was added dropwise a solution of bromine (32 g, 0.2 mol) in chloroform (50 ml). The solution was stirred at 0° C. for 1 hour and at room temperature for 2 hours. Dichloromethane (200 ml) and water (400 ml) were added and the organic phase was washed further with water (400 ml), brine (200 ml) and dried (MgSO$_4$). The solvent was removed and the residue was purified by distillation at reduced pressure to give the title compound. $^1$H NMR (250 MHz, CDCl$_3$) δ 7.38 (1H, d, J 2.1 Hz), 7.13 (1H, dd, J 9.1, 2.1 Hz), 7.03 (1H, d, J 9.1 Hz), and 5.53 (1H, s).

b) 2-Benzyloxy-5-(trifluoromethoxy)bromobenzene

2-Bromo-4-(trifluoromethoxy)phenyl (Description 11a; 5 g, 20 mmol) was dissolved in N,N-dimethylformamide (60 ml), and potassium carbonate (5.4 g, 40 mmol) was added, followed by benzyl bromide (3.5 ml, 30 mmol), and the reaction was stirred at ambient temperature for 15 hours. The reaction was diluted with water (150 ml) and extracted into ethyl acetate (3×60 ml). The combined organic fractions were washed with water (100 ml), brine (100 ml), dried (MgSO$_4$) and evaporated in vacuo. Purification on silica, eluting with 2% and 5% ethyl acetate in hexane gave the title compound as a clear oil (6.7 g, 96%). $^1$H NMR (250 MHz, CDCl$_3$) δ 5.47 (2H, s), 7.23 (1H, d, J 9 Hz), 7.43 (1H, dd J 8.2, 2.9 Hz), and 7.75 (6H, m).

c) (5R,6S)-3-(2-Benzyloxy-5-(trifluoromethoxy)phenyl)-7-(tert-butoxycarbonyl)-6-phenyl-7-aza-1-oxa-spiro[4.5]dec-3-ene The compound of Description 6 (5.75 g), 2-benzyloxy-5-(trifluromethoxy)bromobenzene (3.97 g) and lithium chloride (2.39 g) were suspended in toluene (50 ml). The solution was purged with nitrogen (×3). Tetrakis(triphenylphosphine)palladium(0) (450 mg) was added and the solution was purged with nitrogen (×3). The reaction was heated at 120° C. for 30 hours. The mixture was cooled and filtered. The filtrate was evaporated to dryness. The residue was dissolved in acetonitrile (20 ml) and washed with hexane (30 ml). The product was extracted into acetonitrile (3×20 ml). The acetonitrile fractions were combined and methanolic potassium fluoride was added (5% aq., 3 ml). The solution was filtered and the filtrate evaporated to dryness. The residue was purified on silica using 10% ethyl acetate in hexane, to yield the title compound as an oil (3.88 g) $^1$H NMR (250 MHz, CDCl$_3$) δ 1.28 (1H, m), 1.66 (9H, s), 1.69 (1H, m), 2.04 (1H, m), (2.37 (1H, m) 3.40 (1H, m), 4.43 (1H, drt, J 12.5, 3.9 Hz), 4.94 (1H, dd, J 12.1, 2.1 Hz), 5.25 (1H, dd, J 12.1, 2.02 Hz), 5.62 (3H, m), 6.99 (1H, t, J 2.1 Hz), 7.28 (2H, m), 7.39 (1H, m), 7.57 (5H, m), 7.75 (5H, m).

DESCRIPTION 12

(3S,5R,6S)-7-(tert-Butoxycarbonyl)-3-(2-hydroxy-5-(trifluoromethoxy))phenyl-6-phenyl-7-aza-1-oxa-spiro[4.5]decane The compound of Description 11 (3.88 g) was dissolved in ethyl acetate (15 ml) and methanol (15 ml). Palladium hydroxide on carbon (1.00 g) was added and the suspension was shaken under a hydrogen atmosphere (50 psi) for 72 hours. The suspension was filtered and the filtrate was evaporated to dryness. The product was purified by medium pressure chromatography using 25% ethyl acetate in hexane to yield two isomers: A (3R, 5R, 6S epimer; 191 mg) and B (3S, 5R, 6S epimer; 2.3 g). The major isomer, the title compound, had the following analyses: $^1$H NMR (250 MHz, CDCl$_3$), δ 1.35 (9H, s), 1.74 (3H, m), 2.18 (2H, m), 2.49 (1H, dd, J 13.0 8.9 Hz), 2.81 (1H, m), 3.61 (1H, qn, J 7.0 Hz), 3.93 (2H, m), 4.22 (1H, dd, J 9.1, 6.9 Hz), 5.30 (1H, s), 6.76 (1H, d, J 7.23 Hz), 6.93 (2H, m), 7.29 (3H, m), 7.56 (2H, d, J 6.7 Hz).

DESCRIPTION 13

(3S,5R,6S)-7-(tert-Butoxycarbonyl)-6-phenyl-3-(5-(trifluoromethoxy)-2-(trifluoromethylsulfonyloxy)phenyl)-7-aza-1-oxa-spiro[4.5]decane The compound of Description 12 (1.8 g) was dissolved in pyridine (8 ml) and cooled to 0° C. Trifluoromethanesulphonic anhydride (1.25 ml) was added dropwise. The reaction was stirred at 0° C. for 16 hours. The reaction was diluted with aqueous copper (II) sulphate solution and the product extracted into ethyl acetate (3×50 ml). The combined ethyl acetate fractions were dried (brine, MgSO$_4$) and evaporated to dryness. The residue was purified by flash chromatography on silica eluting with 10% ethyl acetate in hexane to yield the product as a colourless oil. $^1$NMR (250

MHz, CDCl$_3$), δ 1.35 (9H, s), 1.75 (3H, m), 2.11 (2H, m), 2.51 (2H, dd, J 13.2, 8.2 Hz), 2.92 (1H, m), 3.63 (1H, q, J 7.9 Hz), 3.72 (1H, m), 4.00 (1H, d, J 12.7 Hz), 4.24 (1H, dd, J 8.5, 6.6 Hz), 5.17 (1H, s), 7.15 (2H, m), 7.30 (3H, m), 7.53 (2H, d, J 6.9 Hz).

DESCRIPTION 14

(3S,5R,6S)-7-(tert-Butoxycarbonyl)-3-(2-(fur-2-yl)-5-(trifluoromethoxy)phenyl)-6-phenyl-7-aza-1-oxa-spiro[4.5]decane The compound of Description 13 (211 mg), 2-(tributylstannyl)furan (0.16 ml), and bis(diphenylphosphino)ferrocene dichloropalladium(II) catalyst (50 mg) were suspended in dioxane (5 ml) and the reaction purged (vac/N$_2$)(x3) via a firestone valve. The reaction was heated at 110° C. for 16 hours. The solution was filtered to remove the catalyst and the filtrate evaporated to dryness. The residue was dissolved in acetonitrile and the solution washed with hexane. The product was extracted into acetonitrile (3×20 ml). Potassium fluoride (5% in methanol) was added to the combined acetonitrile fractions causing a precipitate to form. The precipitate was removed by filtration, and the filtrate evaporated to dryness. The residue was purified by medium pressure chromatography on silica using 15% ethyl acetate in hexane as eluant to yield the title compound as a yellow oil. MS (ES$^+$) m/z 444 (M$^+$−100)+1, 100%), 488 (M$^+$−56)+1, 80%). $^1$H NMR (250 MHz, CDCl$_3$), δ 1.34 (9H, s), 1.72 (3H, m), 2.09 (1H, m), 2.19 (1H, m), 2.43 (1H, dd, J 12.9, 8.01 Hz), 2.85 (1H, m), 3.72 (1H, q, J 7.8 Hz), 3.82 (1H, m), 3.99 (1H, d, J 12.7 Hz), 4.15 (1H, dd, J 8.4, 6.5 Hz), 5.21 (1H, s), 6.47 (1H, dd, J 3.3, 0.6 Hz), 6.51 (1H, dd, J 3.3, 1.8 Hz), 7.12 (1H, d, J 8.5 Hz), 7.3 (4H, m), 7.53 (4H, m).

DESCRIPTION 15

(5R,6S)-7-(tert-Butoxycarbonyl)-3-(2-(fur-2-yl)-5-(trifluoromethoxy))phenyl-6-phenyl-7-aza-1-oxa-spiro[4.5]dec-3-ene a) 5-(Trifluoromethoxy)-2-(trifluoromethylsulfonyloxy)bromobenzene 2-Bromo-5-(trifluoromethoxy)phenol (10 g) was dissolved in pyridine and the solution was cooled to 0° C.; trifluoromethanesulfonic anhydride (7.2 ml) was added dropwise and the resulting mixture was stirred and allowed to reach room temperature over 2 hours. The mixture was diluted with copper sulfate (aq. 100 ml) and extracted with ethyl acetate (3×20 ml). The organic layer was dried (brine, MgSO$_4$) and concentrated in vacuo and the residue was purified by chromatography on silica using hexane as eluant (13.1 g). $^1$H NMR (250 MHz, CDCl$_3$), δ 7.24–7.29 (1H, m), 7.40 (1H, d, J 12.7 Hz), 7.58 (1H, d, J 2.8 Hz).

b) (5R,6S)-7-(tert-Butoxycarbonyl)-3-(5-(trifluoromethoxy)-2-(trifluoromethylsulfonyloxy)phenyl)-6-phenyl-7-aza-1-oxa-spiro[4.5]dec-3-ene The stannane (Description 19 below) (1.2 g), the bromobenzene described in a) above (778 mg) and lithium chloride (252 mg) were suspended in toluene and the mixture was degassed and purged with nitrogen (x5, firestone valve). Tetrakis(triphenylphosphine)palladium(0) (100 mg) was added and the mixture was repurged with nitrogen. The reaction mixture was heated at reflux overnight. The mixture was diluted with water and the product was extracted with ethyl acetate (3×20 ml). The organic layer was dried (brine, MgSO$_4$) and concentrated in vacuo and the residue was purified by medium pressure chromatography on silica using 10% ethyl acetate in hexane as eluant to afford the compound as a clear oil (800 mg). $^1$H NMR (360 MHz, CDCl$_3$), δ 1.35 (9H, s), 1.80–1.95 (3H, m), 2.10–2.19 (1H, m), 3.12–3.21 (1H, m), 4.11–4.16 (1H, m), 4.51 (1H, dd, J 12.3 2.2 Hz), 4.85 (1H, dd, J 12.2, 2.0 Hz), 5.13 (1H, s), 6.53 (1H, t, J 2.0 Hz), 6.94 (1H, d, J 2.6 Hz), 7.18–7.44 (7H, m).

c) (5R,6R)-7-(tert-Butoxycarbonyl)-3-(2-fur-2-yl-5-(trifluoromethoxy))phenyl-6-phenyl-7-aza-1-oxa-spiro[4.5]dec-3-ene The triflate described in b) above (800 mg), 2-furylboronic acid, lithium chloride (327 mg) and sodium carbonate (50 mg in water, 2.5 ml) were suspended in dimethoxyethane (15 ml) and the mixture was degassed and purged with nitrogen (x5, firestone valve). Bis(triphenylphosphine)palladium dichloride (100 mg) was added and the mixture was repurged with nitrogen. The reaction mixture was heated at reflux overnight. The mixture wad diluted with water and the product was extracted with ethyl acetate (3×20 ml). The organic layer was dried (brine, MgSO$_4$) and concentrated in vacuo and the residue was purified by medium pressure chromatography on silica using 10% ethyl acetate in hexane as eluant to afford the compound as a clear oil (200 mg). $^1$H NMR (250 MHz, CDCl$_3$), δ 1.34 (9H, s), 1.61 (3H, br s), 1.80 (2H, m), 2.12 (1H, m), 3.19 (1H, s), 4.13 (2H, m), 4.19 (1H, dd, J 12.5, 2.2 Hz), 4.55 (1H, dd, J 12.5, 2.0 Hz), 5.09 (1H, s), 5.95 (1H, t, J 2.0 Hz), 6.39 (2H, d, J 8.5 Hz), 6.99 (1H, s), 7.26 (4H, m), 7.61 (1H, d, J 8.6 Hz).

DESCRIPTION 16

(3S,5R,6S)-7-(tert-Butoxycarbonyl)-6-phenyl-3-(2-(thiazol-5-yl)-5-(trifluoromethoxy)phenyl)-7-aza-1-oxa-spiro[4.5]decane The compound of Description 13 (200 mg) and 5-(tributylstannyl)-1,3-thiazole (Synthesis 1986, 757) (144 mg) and lithium chloride (80 mg) were suspended in dioxane (5 ml) and the mixture was degassed and purged with nitrogen (x5, firestone valve). Tetrakis(triphenylphosphine)palladium(0) (50 mg) was added and the mixture was repurged with nitrogen. The reaction mixture was heated at reflux for 4 hours. The mixture was diluted with water and the product was extracted with ethyl acetate (3×20 ml). The organic layer was dried (brine, MgSO$_4$) and concentrated in vacuo and the residue was purified by medium pressure chromatography on silica using 10% ethyl acetate in hexane as eluant to afford the compound as a clear oil (120 mg, 67%). $^1$H NMR (250 MHz, CDCl$_3$) δ 1.37 (9H, s), 1.67 (3H, m), 2.03 (1H, m), 2.09 (1H, dd, J 13.2, 8.6 Hz), 2.36 (1H, dd, J 13.2, 8.5 Hz), 2.89 (1H, m), 3.52 (1H, qn, J 8.4 Hz), 3.66 (1H, t, J 8.3 Hz), 4.04 (1H, d, J 12.7 Hz), 4.07 (1H, dd, J 8.5, 6.7 Hz), 5.22 (1H, s), 6.79 (1H, d, J 8.7 Hz), 7.10 (1H, s), 7.30 (5H, m), 7.55 (2H, d, J 7.2 Hz), 7.76 (1H, s)

DESCRIPTION 17

(3S,5R,6S)-7-(tert-Butoxycarbonyl)-6-phenyl-3-(2-(thien-2-yl)-5-(trifluoromethoxy)phenyl)-7-aza-1-oxa-spiro[4.5]decane This compound was prepared from the Stille coupling of the compound of Description 13 and 2-(tributylstannyl)thiophene according to the method illustrated in Description 16. MS (ES$^+$) m/z 460 (M$^+$+1 (−56), 100%), 504 (M$^+$+1, 70%).

DESCRIPTION 18

(2S,3R)-1-tert-Butoxycarbonyl-3-(3-hydroxypyn-1-yl)-2-phenylpiperidin-3-ol

O-Trimethylsilylpropargyl alcohol (24.51 ml, 20.47 g, 160 ml) was added slowly to a cooled (−10° C.) solution of ethylmagnesium bromide (1M in tetrahydrofuran, 160 ml, 160 mmol). The mixture was stirred at 0° C. for 20 minutes, then at room temperature for 2 hours. The mixture was cooled to −10° C. and a solution of (2S)-1-tert-butoxycarbonyl-2-phenylpiperidin-3-one (Description 1; 42.3 g) in tetrahydrofuran (200 ml) was added dropwise over 30 minutes (internal temperature below −5° C.). The mixture was stirred at room temperature for 14 hours, poured into water (300 ml) and saturated aqueous ammonium chloride (300 ml) and extracted with ethyl acetate (2×300 ml). The combined organic fractions were washed with brine (300 ml), dried ($MgSO_4$) and the solvent was evaporated under reduced pressure. The residue was dissolved in ethyl acetate (500 ml) and a solution of tetrabutylammonium fluoride (1M in tetrahydrofuran, 160 ml, 160 mmol) was added dropwise. The mixture was stirred at room temperature for 30 minutes, water (300 ml) was added, and the layers were separated. The aqueous layer was extracted with ethyl acetate (2×300 ml) and the combined organic fractions were washed with water (300 ml) and brine (300 ml), dried ($MgSO_4$) and the solvent was evaporated under reduced pressure to give the crude title compound as an orange oil (45 g). The crude material was purified by flash column chromatography on silica gel, eluting with hexane/EtOAc (90:10 increasing to 25:75) to give the title compound as an amber oil (32.2 g). $^1H$ NMR ($CDCl_3$) δ 7.53–7.55 (2H, m), 7.19–7.35 (3H, m), 5.56 (1H, s), 4.27 (2H, s), 3.99–4.03 (1H, m), 3.25 (1H, br s), 2.77–2.81 (1H, m), 2.77 (1H, br s), 2.12–2.20 (1H, m), 1.91–1.99 (2H, m), 1.77–1.83 (1H, m), and 1.39 (9H, s).

DESCRIPTION 19

(5R,6S)-7-(tert-Butoxycarbonyl)-6-phenyl-3-(tributylstannyl)-7-aza-1-oxa-spiro[4.5]dec-3-ene Crude (2S,3R)-1-tert-butoxycarbonyl-3-(3-hydroxypropyn-1-yl)-2-phenylpiperidin-3-ol (Description 18; 45 g) was dissolved in toluene (750 ml) and degassed with nitrogen. Tetrakis(triphenylphosphine) palladium (0) (2.30 g, 2.0 mmol) in toluene (600 ml) was added and the mixture was degassed. Tributyltin hydride (35.78 ml, 38.71 g, 133 mmol) was added dropwise over 15 minutes, with stirring and cooling (internal temperature below 25° C.). The mixture was stirred at room temperature for 1 hour, then the solvent was evaporated under reduced pressure. The residue was dissolved in tetrahydrofuran (600 ml) and triphenylphosphine (34.88 g, 133 mmol) was added. A solution of diethyl azodicarboxylate (20.94 ml, 23.16 g, 133 mmol) in tetrahydrofuran (150 ml) was added dropwise with stirring and cooling and the mixture was stirred at room temperature for 1 hour. The solvent was evaporated under reduced pressure, acetonitrile (600 ml) was added and the mixture was extracted with hexane (8×150 ml). The hexane fractions were combined and the solvent was evaporated under reduced pressure. The residue was purified by flash column chromatography on silica gel, eluting with dichloromethane/ethyl acetate (100:0 increasing to 99:1) to give the title compound as a yellow oil (53.64 g, 67% from (2s,3S)-1-tert-butoxycarbonyl-3-hydroxy-2-phenylpiperidine). $^1H$ NMR ($CDCl_3$) δ 7.38–7.40 (2H, m), 7.15–7.25 (3H, m), 5.96 (1H, t, J 2.3 Hz), 4.93 (1H, s), 4.63 (1H, dd, J 2.23, 12.9 Hz), 4.22 (1H, dd, J 2.23, 12.9 Hz), 4.09–4.14 (1H, m), 3.09–3.17 (1H, m), 1.95–1.99 (1H, m), 1.83–1.86 (1H, m), 1.72–1.76 (2H, m), 1.40–1.51 (6H, m), 1.38 (9H, s), 1.25–1.32 (6H, m), and 0.86–0.99 (15H, m).

DESCRIPTION 20

Z-(2S,3R)-1-tert-Butoxycarbonyl-3-(3-hydroxyprop-1-en-1-yl)-2-phenylpiperidin-3-ol Palladium on calcium carbonate, poisoned with lead (Lindlar catalyst, 2 g) was added to a solution of (2S,3R)-1-tert-butoxycarbonyl-3-(3-hydroxypropyn-1-yl)-2-phenylpiperidin-3-ol (Description 18; 32 g, 96.6 mmol) in ethyl acetate (300 ml) and the mixture was stirred under hydrogen (1 atm.) for 4 hours. The mixture was filtered and the solvent was evaporated under reduced pressure to give the title compound as an oil (32 g, 100%). $^1H$ NMR (360 MHz, $CDCl_3$) δ 7.42 (2H, d, J 7.6 Hz), 7.35–7.25 (3H, m), 5.83 (1H, d, J 12.3 Hz), 5.68 (1H, dt, J 12.3, 6.0 Hz), 5.06 (1H, s), 4.27 (1H, m), 4.12 (2H, m), 3.32 (1H, m), 3.13 (1H, s), 2.28 (1H, t, J 5.9 Hz), 2.02 (1H, m), 1.92–1.78 (3H, m), and 1.32 (9H, s). m/z ($ES^+$) 334 (M+1).

DESCRIPTION 21

(5R,6S)-7-(tert-Butoxycarbonyl)-6-phenyl-7-aza-1-oxa-spiro[4.5]dec-3-ene

Diethyl azodicarboxylate (18.2 ml, 115 mmol) in THF (100 ml) was added dropwise to a solution of Z-(2S,3R)-1-tert-butoxycarbonyl-3-(3-hydroxyprop-1-en-1-yl)-2-phenylpiperidin-3-ol (Description 20; 32 g, 96 mmol) and triphenylphosphine (30.2 g, 115 mmol) in THF (700 ml). The mixture was stirred at 0° C. for 30 minutes then at room temperature for 1.5 hours. The solvent was evaporated under reduced pressure and the residue was purified by flash column chromatography on silica gel, eluting with hexane/ethyl acetate (95:5 increasing to 80:20) to give the title compound as a colorless solid (23.4 g, 77%). MS ($ES^+$) m/z 316 ($M^+$+1, 100%). $^1H$ NMR ($CDCl_3$) δ 7.45 (2H, d, J 7.4 Hz), 7.27 (2H, t, J 7.4 Hz), 7.20 (1H, t, J 7.4 Hz), 6.03 (1H, dt, J 6.1, 2.0 Hz), 5.68 (1H, dt, J 6.1, 2.0 Hz), 5.06 (1H, s), 4.61 (1H, dt, J 13.1, 2.0 Hz), 4.32 (1H, dt, J 13.1, 2.0 Hz), 4.08 (1H, m), 3.05 (1H, m), 2.05 (1H, m), 1.75 (3H, m), and 1.37 (9H, s).

DESCRIPTION 22

(3R,5R,6S)-3-(2-Benzyloxy-5-(trifluoromethoxy)phenyl)-7-(tert-butoxycarbonyl)-6-phenyl-7-aza-1-oxa-spiro[4.5]decane a) 2-Benzyloxy-5-(trifluoromethoxy)benzene Benzyl bromide (66.17 ml, 95.35 g, 0.56 mol) was added to a mixture of 4-(trifluoromethoxy)phenol (90.26 g, 0.51 mol) and potassium carbonate (140.97 g, 1.2 mol) in dimethylformamide (160 ml) and the mixture was stirred at room temperature for 72 hours. The mixture was poured into water (1.5 liters) and extracted with ethyl acetate (3×500 ml). The combined organic fractions were washed with aqueous sodium carbonate (saturated, 500 ml), dried ($MgSO_4$) and the solvent was evaporated under reduced pressure to give the title compound as a colorless solid (133.5 g, 99%). $^1H$ NMR (360 MHz, $CDCl_3$) δ 7.39 (5H, m), 7.14 (2H, d, J 9.0 Hz), 6.95 (2H, d, J 9.0 Hz), and 5.05 (2H, s).

b) 2-Benzyloxy-5-(trifluoromethoxy)iodobenzene

Iodine (71.96 g, 0.28 mol) in chloroform was added dropwise to a mixture of 2-benzyloxy-5-(trifluoromethoxy)

benzene (Description 22a, 73.06 g, 0.27 mol) and silver trifluoroacetate (71.57 g, 0.32 mol) in dichloromethane and the mixture was stirred at room temperature for 18 hours. The mixture was filtered through celite, washed with aqueous sodium thiosulfate (5%, 2×2 liters), dried (MgSO$_4$) and the solvent was evaporated under reduced pressure. The residue was purified by flash column chromatography on silica gel, eluting with hexane/EtOAc, to give the title compound as a colorless oil (108.03 g), containing 11% unreacted 2-benzyloxy-5-(trifluoromethoxy)iodobenzene. $^1$H NMR (360 MHz, CDCl$_3$) δ 7.67 (1H, d, J 2.8 Hz), 7.40 (5H, m), 7.16 (1H, dd, J 8.9, 2.8 Hz), 6.82 (1H, d, J 8.9 Hz), and 5.14 (2H, s).

c) (3R,5R,6S)-3-(2-Benzyloxy-5-(trifluoromethoxy) phenyl)-7-(tert-butoxycarbonyl)-6-phenyl-7-aza-1-oxa-spiro[4.5]decane A mixture of 2-benzyloxy-5-(trifluoromethoxy) iodobenzene (Description 22b, 21.8 g, 55.2 mmol), (5R,6S)-7-(tert-butoxycarbonyl)-6-phenyl-7-aza-1-oxa-spiro[4.5] dec-3-ene (Description 21, 7.0 g, 22.1 mmol), tetra-n-butylammonium chloride (6.18 g, 22.2 mmol), lithium chloride (9.35 g, 0.22 mol) and potassium formate (5.64 g, 67.0 mmol) in dimethylformamide (100 ml) was degassed with a firestone valve (x5) and purged with nitrogen. Palladium acetate (491 mg, 2.2 mmol) was added and the mixture was degassed with a firestone valve (x5). The mixture was stirred at 60° C. for 15 hours, then further 2-benzyloxy-5-(trifluoromethoxy)iodobenzene (Description 22b, 4.32 g, 11.0 mmol), potassium formate (2.78 g, 33.5 mmol) and palladium acetate 260 mg, 1.1 mmol) were added. The mixture was stirred at 60° C. for 22 hours, cooled and filtered. The solvent was evaporated under reduced pressure, water (600 ml) was added and the mixture was extracted with ethyl acetate (2×300 ml). The combined organic fractions were washed with brine (300 ml), dried (MgSO$_4$) and the solvent was evaporated under reduced pressure. The residue was purified by flash column chromatography on silica gel, eluting with hexane/CH$_2$Cl$_2$ (75:25 increasing to 0:100) then CH$_2$Cl$_2$/EtOAc (95:5), to give the title compound (9.42 g, 73%). $^1$H NMR (360 MHz, CDCl$_3$) δ 7.56 (2H, d, J 7.7 Hz), 7.40–7.20 (8H, m), 7.14 (1H, d, J 2.0 Hz), 7.00 (1H, dd, J 8.9, 2.0 Hz), 6.88 (1H, d, J 8.9 Hz), 5.30 (1H, s), 5.08 (2H, s), 4.27 (1H, m), 3.97 (1H, m), 3.87 (2H, m), 2.78 (1H, m), 2.56 (1H, m), 2.15 (1H, m), 1.96 (1H, m), 1.67 (3H, m), and 1.42 (9H, s).

DESCRIPTION 23

(3R,5R,6S)-7-(tert-Butoxycarbonyl)-3-(2-hydroxy-5-(trifluoromethoxy)phenyl)-6-phenyl-7-aza-1-oxa-spiro[4.5]decane Palladium on carbon (10%, 0.59 g) was added to a solution of the compound of Description 22c (6.10 g, 10.5 mmol) in methanol-water (99:1, 200 ml) and the mixture was stirred under hydrogen (50 psi.) for 72 hours. The mixture was filtered, washing with ethanol, and the solvent was evaporated under reduced pressure. The residue was purified by flash column chromatography on silica gel, eluting with CH$_2$Cl$_2$/EtOAc (99:1 increasing to 90:10) to give the title compound. $^1$H NMR (360 MHz, CDCl$_3$) δ 7.70 (2H, d, J 7.3 Hz), 7.33 (2H, t, J 7.3 Hz), 7.26 (1H, d, J 7.3 Hz), 7.05 (1H, br s), 6.96 (2H, m), 6.82 (1H, d, J 9.4 Hz), 5.43 (1H, s), 4.27 (1H, m), 4.01 (1H, m), 3.95 (1H, m), 3.73 (1H, m), 2.73 (2H, m), 2.33 (1H, m), 1.87–1.58 (4H, m), and 1.50 (9H, s).

DESCRIPTION 24

(3R,5R,6S)-7-(tert-Butoxycarbonyl)-6-phenyl-3-(5-(trifluoromethoxy)-2-(trifluoromethylsulfonyloxy) phenyl)-7-aza-1-oxa-spiro[4.5]decane Trifluoromethanesulphonic anhydride (0.68 ml) was added dropwise to a stirred, cooled (0° C.) solution the compound of Description 23 (1 g) in pyridine (4 ml). The mixture was allowed to warm to room temperature and stirred for 16 hours. Further trifluoromethanesulphonic anhydride (0.34 ml) was added and the mixture was stirred at room temperature for 2 hours. Aqueous copper (II) sulphate was added and the mixture was extracted with ethyl acetate (3×50 ml). The combined organic fractions were washed with brine, dried (MgSO$_4$) and the solvent was evaporated under reduced pressure. The residue was purified by MPLC on silica gel, eluting with hexane/EtOAc (90:10) to give the title compound as a colourless oil. $^1$H NMR (360 MHz, CDCl$_3$) δ 1.43 (9H, s), 1.78 (3H, m), 2.25 (2H, m), 2.78 (2H, m), 385 (2H, m), 4.02 (1H, dd, J 13.7 Hz), 4.27 (1H, dd, J 8.7, 6.9 Hz), 5.30 (1H, s), 7.27 (1H, m), 7.31 (5H, m), and 7.57 (2H, d, J 7.6 Hz).

DESCRIPTION 25

(3R,5R,6S)-7-(tert-Butoxycarbonyl)-3-(2-(fur-3-yl)-5-(trifluoromethoxy)phenyl)-6-phenyl-7-aza-1-oxa-spiro[4.5]decane a) 3-(Tributylstannyl)furan 3-Bromofuran (1.23 ml) was dissolved in diethyl ether (15 ml) and cooled to −76° C. Butyllithium (8.5 ml, 1.6M in hexane) was added dropwise ensuring the temperature remained below −60° C. After stirring for 15 minutes, tributyltin chloride (3.69 ml) was added. The reaction was stirred at −76° C. for 1 hour. The reaction was diluted with aqueous sodium hydrogencarbonate (20 ml) and the product extracted with diethyl ether (3×20 ml). The combined organic fractions were dried (brine, MgSO$_4$) and concentrated in vacuo. The residue was purified by chromatography on silica eluting with hexane to yield the title compound as a colourless oil. $^1$H NMR (CDCl$_3$, 360 MHz), δ 0.91 (9H, t, J 8.9 Hz), 1.03 (6H, t, J 10.4 Hz), 1.34 (6H, sx, J 7.3 Hz), 1.58 (6H, m), 6.35 (1H, d, J 1.5 Hz), 7.23 (1H, s), 7.56 (1H, t, J 1.4 Hz).

b) (3R,5R,6S)-7-(tert-Butoxycarbonyl)-3-(2-(fur-3-yl)-5-(trifluoromethoxy)phenyl)-6-phenyl-7-aza-1-oxa-spiro[4.5] decane The triflate of Description 24, (300 mg), 3-(tributylstannyl)furan (205 mg), lithium chloride (121 mg) and tetrakis(triphenylphosphine) palladium(0) (50 mg) were dissolved in dioxane (5 ml). The reaction was purged (5x vac/N$_2$) and heated at 110° C. for 16 hours. The catalyst was removed by filtration and the filtrate concentrated in vacuo. The residue was dissolved in acetonitrile (10 ml) and the solution washed with hexane (20 ml). The product was extracted with acetonitrile (3×10 ml). To the combined acetonitrile fractions was added potassium fluoride (3 ml×5% methanolic soln.). The precipitate formed was removed by filtration. The filtrated was concentrated in vacuo and the residue purified by chromatography on silica eluting with 10% ethyl acetate in hexane to yield the title compound as an oil. MS (ES$^+$) m/z 444 (M+H−100, 65%), 488 (M+H−56, 100%), 544 (M+H, 2%). $^1$H NMR (CDCl$_3$, 360 MHz), δ 1.49 (9H, s), 1.72 (1H, m), 1.84 (2H, m), 2.28 (1H, td, J 12.2 Hz), 2.63 (1H, dd, J 12.3, 8.0 Hz), 2.75 (1H, td, J 12.2, 5.0 Hz), 3.89 (3H, m), 3.97 (1H, d, J 10.2 Hz), 4.13 (1H, m), 5.23 (1H, s), 6.46 (1H, s), 7.8 (1H, d, J 8.2 Hz), 7.27 (5H, m), 7.47 (1H, s), 7.50 (1H, s), 7.55 (2H, d, J 7.8 Hz).

DESCRIPTION 26

(3R,5R,6S)-7-tert-Butoxycarbonyl-6-phenyl-3-(2-(pyrid-2-yl)-5-(trifluoromethoxy)phenyl)-7-aza-1-oxa-spiro[4.5]decane This compound was prepared from the Stille coupling of the compound of Description 24 and 2-(tributylstannyl)

pyridine according to the method illustrated in Description 25. ¹H NMR (CDCl₃, 360 MHz), δ 1.39 (9H, s), 1.61 (1H, m), 1.69 (1H, m), 1.79 (1H, d, J 12.7 Hz), 1.88 (1H, dd, J 12.9, 9.3 Hz), 2.48 (1H, m), 2.63 (1H, dd, J 12.9, 8.3 Hz), 2.74 (1H, td, J 12.9. 3.8 Hz), 3.76 (1H, qn, J 7.8 Hz), 3.92 (2H, m), 4.14 (1H, t, J 7.6 Hz), 5.15 (1H, s), 7.17 (1H, d, J 10.1 Hz), 7.25 (1H, d, J 11.8 Hz), 7.30 (3H, m), 7.37 (2H, m), 7.53 (2H, d, J 7.7 Hz), 7.79 (1H, dd, J 9.2, 1.6 Hz), 8.40 (1H, d, J 7.9 Hz), 8.64 (1H, m)

DESCRIPTION 27

(3R,5R,6S)-7-tert-Butoxycarbonyl-6-phenyl-3-(2-(pyrid-3-yl)-5-(trifluoromethoxy)phenyl)-7-aza-1-oxa-spiro[4.5]decane This compound was prepared from the Stille coupling of the compound of Description 24 and 3-(tributylstannyl) pyridine according to the method illustrated in Description 25. MS (ES⁺) m/z 555 (M⁺+1, 100%) ¹H NMR (360 MHz, CDCl₃) δ 1.38 (9H, s), 1.49–1.89 (4H, m), 2.25 (1H, dt, J 13.0, 5.0 Hz), 2.58 (1H, dd, J 13.0, 8.4 Hz), 2.74 (1H, dt, J 13.0, 3.7 Hz), 3.52 (1H, qn, J 8.4 Hz), 3.88 (1H, t, J 8.87 Hz), 3.95 (1H, mc), 4.09 (1H, t, J 7.5 Hz), 5.10 (1H, s), 7.15–7.31 (5H, m), 7.37–7.42 (2H, m), 7.49 (2H, d, J 7.8 Hz), 7.60 (1H, dd, J 7.76 1.8 Hz), 8.54 (1H, s), (1H, d, J 4.0 Hz).

DESCRIPTION 28

(3R,5R,6S)-7-tert-Butoxycarbonyl-6-phenyl-3-(2-(pyrid-4-yl)-5-(trifluoromethoxy)phenyl)-7-aza-1-oxa-spiro[4.5]decane This compound was prepared from the Stille coupling of the compound of Description 24 and 4-(trimethylstannyl) pyridine according to the method illustrated in Description 25. MS (ES⁺) m/z 555 (M⁺+1, 100%) ¹H NMR (250 MHz, CDCl₃), δ 1.38 (9H, s), 1.58–1.89 (4H, m), 2.28 (1H, dt, J 12.9, 5.0 Hz), 2.60 (1H, dd, J 12.9, 6.5 Hz), 2.60 (1H, dt, J 12.9, 3.7 Hz), 3.54 (1H, qn, J 8.0 Hz), 3.43–3.60 (2H, m), 4.10 (1H, t, J 7.2 Hz), 5.12 (1H, s), 7.14–7.31 97H, m), 7.37 (1H, s), 7.50 (2H d, J 7.3 Hz), 8.70 (2H, d, J 7.3 Hz).

DESCRIPTION 29

(3R,5R,6S)-7-tert-Butoxycarbonyl-3-(2-(oxazol-2-yl)-5-(trifluoromethoxy)phenyl)-6-phenyl-7-aza-1-oxa-spiro[4.5]decane This compound was prepared from the Stille coupling of the compound of Description 24 and 2-(tributylstannyl) oxazole (EP-0 590 970-A) according to the method illustrated in Description 25. MS (ES) m/z 546 (M⁺+1, 60%), 489 (M⁺–56, 100%). ¹H NMR (360 MHz, CDCl₃) δ 1.47 (9H, s), 1.58–1.80 (3H, m), 2.24 (1H, dt, J 13.0, 5.0 Hz), 2.76–2.85 (2H, m), 3.92–4.00 (2H, m), 4.13 (1H, dd, J 9.0, 7.5 Hz), 4.61–4.67 (2H, m), 5.36 (1H, s), 7.17 (1H, dd, J 8.0, 1.1 Hz), 7.22–7.34 (4H, m), 7.40 (1H, d, J 2.0 Hz), 7.60 (2H, d, J 8.5 Hz), 7.78 (1H, s), 7.93 (1H, d, J 8.5 Hz).

DESCRIPTION 30

(3R,5R,6S)-7-tert-Butoxycarbonyl-6-phenyl-3-(2-(pyrazin-2-yl)-5-(trifluoromethoxy)phenyl)-7-aza-1-oxa-spiro[4.5]decane This compound was prepared from the Stille coupling of the compound of Description 24 and 2-(tributylstannyl) pyrazine (Synth. Commun. 1992, 22(12) 1757–62) according to the method illustrated in Description 25. MS (ES) m/z 556 (M⁺+1, 60%), 500 (m⁺–56, 100%), 456 (M⁺–100, 10%). ¹H NMR (250 MHz, CDCl₃) δ 1.39 (9H, s), 1.62–1.94 (4H, m), 2.35 (1H, dt, J 12.5, 5.0 Hz), 2.64–2.81 (2H, m), 3.67–3.79 (1H, m), 3.89–3.98 (1H, m), 4.18 (1H, t, J 7.5 Hz), 5.16 (1H, s), 7.18–7.55 (8H, m), 8.58–8.61 (1H, m), 8.78 (1H, s).

DESCRIPTION 31

(3R,5R,6S)-7-tert-Butoxycarbonyl-6-phenyl-3-(2-(pyrimidin-5-yl)-5-(trifluoromethoxy)phenyl)-7-aza-1-oxa-spiro[4.5]decane This compound was prepared from the Suzuki coupling of the compound of Description 24 and 5-(pyrimidin-yl) boronic acid (Chem. Scr. 1986, 26(2) 305–9) according to the following method: The triflate (Desc. 24, 200 mg), lithium chloride (80 mg), sodium carbonate (1M aq., 1 ml), and 5-(pyrimidin-yl)boronic acid (44 mg) were suspended in DME (5 ml) at room temperature. The mixture was then degassed 5 times and purged with nitrogen before adding tetrakistriphenylphosphine palladium(0) (50 mg, 5 mol %) and repeating the degassing procedure. The mixture was heated at reflux for 48 hours. The mixture was then partitioned between water and ethyl acetate and the organic layer was then washed with brine, dried (MgSO₄), filtered and evaporated, to give a crude oil which was purified by medium pressure chromatography on silica eluting with 30% ethyl acetate in hexane to afford a colourless oil (48% yield). MS (ES) m/z 556 (M⁺+1, 45%), 500 (M⁺–56, 50%). ¹H NMR (250 MHz, CDCl₃) δ 1.47 (9H, s), 1.52–1.96 (4H, m), 2.28 (1H, dt, J 12.5, 5.3 Hz), 2.60 (1H, dd, J 12.5, 8.5 Hz), 2.77 (1H, dd, J 13.0, 3.8 Hz), 3.34–3.52 (1H, m), 3.87–3.99 (2H, m), 4.08–4.16 (1H, m), 5.11 (1H, s), 7.18–7.51 (8H, m), 8.68 (2H, s), 9.28 (1H, s).

DESCRIPTION 32

(3R,5R,6S)-7-(tert-Butoxycarbonyl)-3-(2-(fur-2-yl)-5-(trifluoromethoxy)phenyl)-6-phenyl-7-aza-1-oxa-spiro[4.5]decane This compound was prepared from the Stille coupling of the compound of Description 24 and 2-(tributylstannyl) furan according to the method illustrated in Description 25. MS (ES) m/z 544 (M⁺+1, 80%), 488 (M⁺–56, 100%). ¹H NMR (360 MHz, CDCl₃) δ 1.44 (9H, s), 1.59–1.66 (3H, m), 1.87 (1H, dd, J 13.0, 8.6 Hz), 2.25 (1H, dt, J 13.0, 5.0 Hz), 2.71 (1H, dd, J 13.3, 8.3 Hz), 2.78 (1H, dt, J 13.3, 3.6 Hz), 3.91–4.03 (3H, m), 4.19 (1H, dd, J 7.2, 6.5 Hz), 5.30 (1H, s), 6.50 (2H, s) 7.12 (1H, dd, J 8.6, 1.0 Hz), 7.21–7.33 (4H, m), 7.50–7.59 (4H, m).

DESCRIPTION 33

(3R,5R,6S)-3-[2-(Ethen-1-yl)-5-(trifluoromethoxy)phenyl]-6-phenyl-1-oxa-7-(tert-butoxycarbonyl)aza-spiro[4,5] decane A mixture of the triflate of Description 24 (200 mg), vinyltributyltin (0.11 ml), lithium chloride (80 mg) and tetrakis(triphenylphosphine)palladium (0) (50 mg) in dioxane (5 ml) was degassed using a firestone valve (×5). The mixture was heated at 110° C. for 2 hours, cooled and filtered. The solvent was evaporated under reduced pressure and the residue was dissolved in acetonitrile. The mixture was washed with hexane (30 ml). The mixture was extracted with ethyl acetate (3×30 ml) and the combined organic fractions were washed with brine, dried (MgSO₄) and the solvent was evaporated under reduced pressure. The residue was purified by MPLC on silica gel, eluting with hexane/

EtOAc (85:15) to give the title compound as an oil. ¹H NMR (360 MHz, CDCl₃) d 1.47 (9H, s), 1.62 (3H, m), 1.83 (1H, m), 2.25 (1H, td), 2.63 (1H, dd, J=7.5 Hz), 2.76 (1H, td), 3.82 (1H, q), 3.90 (1H, t, J=8.3 Hz), 3.98 (1H, dd), 4.24 (1H, J=7.3 Hz), 5.36 (2H, m), 5.57 (1H, d, J=16.7 Hz), 6.97 (1H, dd, J=11.0, 16.9 Hz), 7.15 (1H, d), 7.25 (1H, s), 7.33 (1H, m), 7.35 (2H, m), 7.76 (1H, d, J=8.5 Hz), and 7.60 (2H, d, J=7.6 Hz).

DESCRIPTION 34
(3R,5R,6S)-3-(2-Formyl-5-(trifluoromethyoxy)phenyl)-7-(tert-butoxycarbonyl)-6-phenyl-1-oxa-7-aza-spiro[4,5]decane The styrene of description 33 (420 mg) was dissolved in dichloromethane (10 ml) and methanol (4 ml) was added. The reaction was cooled to −76° C. and purged with nitrogen. A steady stream of oxygen was bubbled through the reaction and the reaction was treated with ozone for 1 hour. The reaction was purged with oxygen for 15 minutes followed by nitrogen for 15 minutes. Dimethyl sulphide (0.3 ml) was added and the reaction stirred at room temperature overnight. The reaction was concentrated in vacuo and the residue purified on silica eluted with 15% ethyl acetate in hexane to yield the above compound as an oil. ¹H NMR (CDCl₃, 360 MHz), δ1.48 (9H, s), 1.55 (2H, m), 1.72 (1H, d, J=9.5 Hz), 1.85 (1H, dd, J=13.0 8.4 Hz), 2.25 (1H, m), 2.77 (2H, m), 3.97 (2H, m), 4.27 (1H, dd, J=9.0, 7.2 Hz), 4.53 (1H, qn, J=7.2 Hz), 5.36 (1H, s), 7.26 (2H, m), 7.34 (3H, m), 7.59 (2H, d, J=7.6 Hz), 7.87 (1H, d, J=8.5 Hz), 10.26 (1H, s), MS (EI+) m/z 450 (M+H−56, 15%), 406 (M+H−100, 100%).

DESCRIPTION 35
(3R,5R,6S)-3-(2-Oxazol-5-yl)-5-(trifluoromethoxy)phenyl)-7-(tert-butoxycarbonyl)-6-phenyl-1-oxa-7-aza-spiro[4,5]decane The aldehyde of Description 34 (150 mg), tosylmethyl isocyanide (58 mg) and potassium carbonate (250 mg) were dissolved in methanol (6 ml) and heated at reflux (65° C.) for one hour. The reaction was concentrated in vacuo and the residue dissolved in dichloromethane (10 ml). The solution was washed with water (20 ml) and the product extracted with dichloromethane (3×10 ml). The combined organic fractions were dried (brine, MgSO₄) and concentrated in vacuo. The residue was purified on silica eluted with 20% ethyl acetate in hexane, to yield the title product as an oil. ¹H NMR (CDCl₃, 360 MHz), δ 1.45 (9H, s), 1.55 (2H, m), 1.75 (1H, m), 1.85 (1H, dd, J=12.8, 8.6 Hz), 2.26 (1H, td), 2.73 (1H, dd, J=12.9, 8.1 Hz), 2.77 (1H, dd, J=13.3 Hz), 3.82 (1H, qn), 3.97 (2H, t, J=7.0 Hz), 4.19 (1H, dd, J=7.2, 8.9 Hz), 5.29 (1H, s), 7.16 (1H, d, J=8.3 Hz), 7.24 (2H, m), 7.32 (2H, t, J=7.0 Hz), 7.37 (1H, s), 7.52 (1H, d, J=8.5 Hz), 7.57 (2H, d, J=7.5 Hz), 8.03 (1H, s), M/Z (ES+) 445 (M+H−100, 100%), 489 (M+H−56, 20%), 545 (M+H, 30%).

DESCRIPTION 36
(3R,5R,6S)-3-(2-(5-Methylfur-2-yl)-5-(trifluoromethoxy)phenyl)-7-(tert-butoxycarbonyl)aza-1-oxa-spiro[4,5]decane This compound was prepared from the Stille coupling of the compound of Description 24 and 5-methyl-2-tributylstannylfuran (*Bull. Chim. Sc. Jpn.* 1992, 65, 2366) according to the method illustrated in Description 25. MS (ES) m/z 503 (M⁺H−56, 7%), 458 (M+H−100, 100%), ¹H NMR (360 MHz, CDCl₃) 1.43 (9H, s), 1.58–1.79 (3H, m), 1.88 (1H, dd, J=13.0, 8.3 Hz), 2.24 (1H, dt, J=12.6, 5.0 Hz), 2.37 (1H, s), 2.69 (1H, dd, J=12.6, 8.3 Hz), 2.81 (1H, dt, J=13.3, 4.0 Hz), 3.61–3.64 (1H, m), 3.90–4.06 (3H, m), 4.20 (1H, dd, J=7.9, 7.2 Hz), 5.30 (1H, s), 6.08 (1H, dd, J=2.2, 0.7 Hz), 6.38 (1H, d, J=3.2 Hz), 7.08–7.11 (1H, m), 7.21–7.33 (4H, m), 7.51–7.58 (3H, m).

DESCRIPTION 37
(3R,5R,6S)-3-(2-(5-Methylisoxazol-4-yl)-5-(trifluoromethoxy)phenyl)-6-phenyl-7-(tert-butoxycarbonyl)aza-1-oxa-spiro[4,5]decane This compound was prepared from the Stille coupling of the compound of Description 24 and 5-methyl-3-tributylstannylfuran (*Heterocycles* 1996,43 1303) according to the method illustrated in Description 25. MS (ES) m/z 559 (M⁺+H, 2%), 459 (M+H−100, 100%) ¹H NMR (360 MHz, CDCl₃) d 1.42 (9H, s), 1.58–1.86 (3H, m), 2.19(3H, s), 2.20–2.33 (1H,m), 2.57 (1H, dd, J=12.8, 8.3 Hz), 2.57 (1H, dd, J=12.8, 8.3 Hz), 2.77 (1H, dt, J=13.3, 3.8 Hz), 3.37–3.50 (1H, m), 3.86 (1H, t, J=8.3 Hz), 3.96(1H, dd, J=13.5,4.5), 4.06–4.16 (1H, m), 5.15 (1H, s) 7.12–7.35 (6H, m), 7.50–7.53 (2H, m), 8.31 (1H,s).

DESCRIPTION 38
(3R,5R,6S)-3-(Thiophen-2-yl-5-(trifluoromethoxy)phenyl)-7-(tert-butoxycarbonyl)-6-phenyl-1-oxa-7-aza-spiro[4,5]decane The triflate of Description 24 (300 mg), thiophene-3-boronic acid (74 mg), lithium chloride (121 mg), water (1 ml) and sodium carbonate (152 mg) were suspended in ethylene glycol dimethyl ether (6 ml) and the reaction purged with vacuum/nitrogen, via a firestone valve. Palladium tetrakistriphenylphosphine (50 mg) was added and the reaction purged again (×3). The reaction was heated at reflux for 16 hours. The reaction was filtered and the filtrate concentrated in vacuo. An aqueous work up was performed and the product extracted with ethyl acetate. The combined organic phase was dried (brine, MgSO₄) and concentrated in vacuo. The residue was purified on silica eluted with 5% ethyl acetate in hexane. ¹H NMR (CDCl₃, 360 MHz), δ 1.41 (9H, s), 1.71 (1H, m), 1.84 (2H, m), 2.25 (2H, m), 2.60 (1H, dd, J=12.9, 8.3 Hz), 2.75 (1H, td, J=13.2, 3.7 Hz), 3.75 (1H, qn, J=8.1 Hz), 3.86 (1H, t, J=7.7 Hz), 3.95 (1H, dd, J=13.9 Hz), 4.11 (1H, t, J=8.7 Hz), 5.17 (1H, s), 7.05 (1H, dd, J=6.2, 1.3 Hz), 7.10 (1H, d, J=9.7 Hz), 7.28 (6H, m), 7.40 (1H, dd, J=4.8 Hz), 7.53 (2H, d, J=7.5 Hz). M/Z (ES+) 560 (M+H, 5%), 504 (M+H−56, 100%), 460 (M+H−100, 25%).

EXAMPLE 1
(5R,6S)-3-(5-Methoxy-2-(5-trifluoromethyl)tetrazol-1-yl)phenyl)-6-phenyl-7-aza-1-oxa-spiro[4.5]dec-3-ene (5R,6S)-7-(tert-butoxycarbonyl)-3-(5-methoxy-2-(5-trifluoromethyl)tetrazol-1-yl)phenyl)-6-phenyl-7-aza-1-oxa-spiro[4.5]dec-3-ene (0.5 g, 0.9 mmol; Desc. 8) was dissolved in 3N methanolic HCl (30 ml) and stirred at ambient temperature for 14 hours. The solvent was evaporated in vacuo, and the residue partitioned between aqueous saturated potassium carbonate (50 ml) and ethyl acetate (50 ml). The organic layer was washed with brine (50 ml), dried over magnesium sulphate and the solvent removed in vacuo. Medium pressure chromatography on silica eluting with 10% methanol/dichloromethane afforded the title compound as a clear oil (350 mg), 85%) MS (ES⁺) m/z 458 (M⁺+H, 100%). ¹H NMR (250 MHz, CDCl₃) δ 1.56 (3H, m), 1.95 (1H, m), 2.69 (1H, dt, J 2.7 Hz, J 12.5 Hz), 2.83 (1H, broad s), 3.21 (1H, m) 3.51 (1H, s), 3.80 (1H, s) 4.15 (1H, dd, J 2.2 Hz, J 12.3 Hz), 4.42 (1H, dd, J 2.2 Hz, J 12.3 Hz), 4.92 (1H, t, J 2.1 Hz), 6.27 (1H, d, J 2.8 Hz), 6.88 (1H, dd, J 2.8 Hz, J 8.8 Hz), 7.17 (1H, d, J 8.8 Hz), 7.25 (5H, m).

EXAMPLE 2

(3S,5R,6S)-3-(5-Methoxy-2-(5-(trifluoromethyl)tetrazol-1-yl)phenyl)-6-phenyl-7-aza-1-oxa-spiro[4.5]decane (3S,5R,6S)-3-(5-Methoxy-2-(5-trifluoromethyl)tetrazol-1-yl)phenyl-6-phenyl-7-aza-1-oxa-spiro[4.5]dec-3-ene (0.35 g, 0.7 mmol; Ex.1) was dissolved in methanol (10 ml) and glacial acetic acid (1 ml) and 10% palladium hydroxide/carbon was added. The reaction mixture was hydrogenated at 40 psi for 15 hours. The solution was filtered and evaporated in vacuo. The residue was partitioned between aqueous saturated potassium carbonate (50 ml) and ethyl acetate (50 ml). The organic layer was washed with brine (50 ml), dried over magnesium sulphate and the solvent evaporated in vacuo. Medium pressure chromatography eluting with 10% methanol/dichloromethane afforded the title compound (105 mg, 34%). MS (ES$^+$) m/z 460 (M$^+$+H, 100%). $^1$H NMR (250 MHz, CDCl$_3$) δ 1.45 (1H, dt, J 13.2 Hz, J 3.9 Hz), 1.51 (1H, m), 1.81 (2H, t, J 10.5 Hz), 1.94 (2H, m), 2.55 (1H, m), 2.77 (1H, dt, J 12.4 Hz, J 2.8 Hz), 3.20 (1H, m), 3.27 (1H, q, J 9.1 Hz), 3.59 (3H, s), 3.69 (1H, s), 3.91 (1H, t, J 7.5 Hz), 5.87 (1H, d, J 2.7 Hz), 6.78 (1H, dd, J 8.8 Hz, J 2.7 Hz), 7.04 (1H, d, J 8.8 Hz), 7.35 (3H, m) 7.53 (2H, m).

EXAMPLE 3

(5R,6S)-3-(5-Methoxy-2-tetrazol-1-yl)phenyl-6-phenyl-7-aza-1-oxa-spiro[4.5]dec-3-ene This compound was prepared and purified from the compound of Description 10 according to the method of Example 1, to afford the title compound as a white foam (170 mg, 55%) m/z (CI$^+$) 390 (M$^+$+H, 100%). $^1$H NMR (360 MHz, CDCl$_3$) δ 1.60 (2H, m), 1.76 (1H, m), 1.95 (1H, m), 2.62 (1H, broad s), 2.73 (1H, dt, J 2.6 Hz, J 12.7 Hz), 3.21 (1H, m), 3.63 (1H, s), 3.80 (3H, s), 4.0 (1H, dd, J 2.2 Hz, J 12.5 Hz), 4.47 (1H, dd, J 2.2 Hz, J 12.5 Hz), 5.02 (1H, t, J 2.1 Hz), 6.42 (1H, d, J 2.8 Hz), 6.88 (1H, dd, J 2.9 Hz, J 8.8 Hz), 7.20 (1H, d, J 8.8 Hz), 7.30 (5H, m), 8.04 (1H, s).

EXAMPLE 4

(3S,5R,6S)-3-(5-Methoxy-2-(tetrazol-1-yl)phenyl)-6-phenyl-7-aza-1-oxa-spiro[4.5]decane hydrochloride This compound was prepared from the product of Example 3 according to the procedure described in Example 2 to afford the title compound as its free base. The hydrochloride salt was made and recrystallized from hot ethyl acetate/methanol to afford the final compound as a white solid (50 mg). MS (ES$^+$) m/z 392 (M$^+$+H, 100%). $^1$H NMR (360 MHz, d$_6$-DMSO) δ 1.70 (4H, m), 1.92 (1H, m), 3.00 (1H, m), 3.18 (3H, m) 3.62 (3H, s), 3.94 (1H, t, J 8.0 Hz), 4.48 (1H, d, J 11.2 Hz), 5.85 (1H, d, J 2.6 Hz), 6.93 (1H, dd, J 2.8 Hz, J 8.8 Hz), 7.37 (1H, d, J 8.8 Hz), 7.54 (5H, m), 9.71 (1H, s).

EXAMPLE 5

(5R,6S)-3-(Fur-2-yl)-5-(trifluoromethoxy)phenyl)-6-phenyl-7-aza-1-oxa-spiro[4.5]dec-3-ene This compound was prepared from the compound of Description 15 according to the method illustrated in Example 1. MS (ES$^+$) m/z 442 (M$^+$+1, 100%). $^1$H NMR (250 MHz, CDCl$_3$), δ1.78 (4H, m), 2.83 (1H, td, J 12.1 Hz), 3.27 (1H, dd, J 13.4 Hz), 3.78 (1H, s), 4.12 (2H, m), 4.47 (1H, dd, J 12.3, 2.1 Hz), 5.61 (1H, t, J 2.12 Hz), 5.91 (1H, d, J 3.4 Hz), 6.32 (1H, dd, J 3.4, 1.8 Hz), 6.49 (1H, s), 7.11 (1H, d, J 8.6 Hz), 7.28 (3H, m), 7.39 (2H, m), 7.57 (1H, d, J 8.7 Hz).

EXAMPLE 6

(3S,5R,6S)-3-(2-Fur-2-yl)-5-(trifluoromethoxy)phenyl)-6-phenyl-7-aza-1-oxa-spiro[4.5]decane The compound of Description 14 (52 mg) was dissolved in a solution of methanolic hydrogen chloride (20 ml, 2M) and stirred at room temperature for 2 hours. The reaction was evaporated to dryness and the residue was recrystallised from hot ethyl acetate to yield the title compound. MS (ES$^+$) m/z 444 (M$^+$+1, 100%). $^1$H NMR (MeOD, 500 MHz), δ 1.87 (3H, m), 2.12 (1H, d, J 13.7 Hz), 2.18 (1H, dd, J 12.9, 4.8 Hz), 2.26 (1H, m), 3.24 (1H, td, J 10.1, 2.7 Hz), 3.43 (2H, m), 4.03 (1H, qn, J 10.8 Hz), 4.20 (1H, t, J 8.2 Hz), 4.68 (1H, s), 6.13 (1H, s), 6.58 (2H, m), 7.15 (1H, d, J 7.5 Hz), 7.48 (1H, d, J 8.6 Hz), 7.57 (5H, m), 7.66 (1H, s).

EXAMPLE 7

(3S,5R,6S)-6-Phenyl-3-(2-(thiazol-2-yl)-5-(trifluoromethoxy)phenyl)-7-aza-1-oxa-spiro[4.5]decane The compound of Description 16 was deprotected according to the method illustrated in Example 6 to afford the title compound as the hydrochloride salt. MS (ES$^+$) m/z 461 (M+H, 100%) $^1$H NMR (500 MHz, CDCl$_3$), δ 1.53 (1H, t, J 10.5 Hz), 1.67 (1H, d, J 14.0 Hz), 1.85 (4H, m), 2.35 (1H, d, J 13.6 Hz), 2.85 (1H, d, J 11.1 Hz), 3.26 (1H, t, J 9.2 Hz), 3.41 (1H, d, J 11.0 Hz), 3.52 (1H, t, J 8.9 Hz), 3.99 (2H, d, J 8.0 Hz), 5.89 (1H, s), 6.98 (1H, d, J 8.3 Hz), 7.22 (1H, d, J 8.5 Hz), 7.37 (2H, t, J 7.5 Hz), 7.46 (1H, t, J 7.3 Hz), 7.64 (2H, m), 9.36 (1H, s), 10.32 (1H, s).

EXAMPLE 8

(3S,5R,6S)-6-Phenyl-3-(2-(thien-2-yl)-5-(trifluoromethoxy)phenyl)-7-aza-1-oxa-spiro[4.5]decane The compound of Description 17 was deprotected according to the method illustrated in Example 6 to afford the title compound as the hydrochloride salt. MS (ES$^+$) m/z 461 (M$^+$+1, 100%). $^1$H NMR (250 MHz, CDCl$_3$) δ 1.52 (1H, t, J 10.9 Hz), 1.59 (2H, s), 1.65 (1H, d, J 14.2 Hz), 1.83 (1H, t, J 11.4 Hz), 1.92 (2H, t, J 12.8 Hz), 2.35 (1H, d, J 13.8 Hz), 2.85 (1H, d, J 11.6 Hz), 3.24 (1H, t, J 9.2 Hz), 3.42 (1H, d, J 11.2 Hz), 3.68 (1H, qn, J 10.0 Hz), 4.00 (2H, q, J 8.3 Hz), 5.88 (1H, s), 6.86 (1H, s), 6.94 (1H, d, J 8.2 Hz), 7.06 (1H, t, J 3.5 Hz), 7.24 (1H, t, J 6.5 Hz), 7.37 (2H, m), 7.46 (1H, t, J 7.4 Hz), 7.63 (1H, br s).

EXAMPLE 9

(3R,5R,6S)-3-(2-(Fur-3-yl)-5-(trifluoromethoxy)phenyl)-6-phenyl-7-aza-1-oxa-spiro[4.5]decane The compound of Description 25 (50 mg) was dissolved in dichloromethane (23 ml) and trifluoroacetic acid (1ml) was added. The reaction was stirred at room temperature for 1 hour. The reaction was diluted with aqueous sodium hydrogencarbonate (10 ml) and the product extracted with dichloromethane. The combined dichloromethane fractions were dried (brine, MgSO$_4$) and concentrated in vacuo. The residue was purified by medium pressure chromatography on silica eluting with 10% methanol in dichloromethane to afford the free base as an oil: $^1$H NMR (CDCl$_3$, 360 MHz), δ 1.59 (2H, m), 2.12 (3H, m), 2.45 (1H, m), 2.77 (1H, t, J 10.6 Hz), 3.23 (1H, d, J 9.8 Hz), 3.50 (1H, d, J 15.2 Hz), 3.56 (1H, d, J 10.4 Hz), 3.88 (1H, t, J 8.0 Hz), 5.98 (1H, s), 6.93 (1H, s), 7.01 (1H, d, J 9.1 Hz), 7.07 (1H, s), 7.11 (1H, d, J 8.4 Hz), 7.24 (4H, m), 7.36 (3H, m). The free base (30 mg) was dissolved in ethyl acetate (5 ml) and hydrochloric acid in methanol (2 ml), 1M) was added. The reaction was evaporated to dryness to yield a solid. The solid was recrystallised from hot ethyl acetate to yield the product as a crystalline solid. MS (ES$^+$) m/z 444, (M+H, 100%). $^1$H NMR (CDCl$_3$, 360 MHz), δ 1.69 (3H, m), 2.10 (2H, m), 2.35

(2H, m), 2.79 (1H, td, J 11.8 Hz), 3.33 (1H, d, J 11.9 Hz), 3.53 (1H, t, J 10.3 Hz), 3.81 (1H, s), 3.93 (1H, t, J 8.1 Hz), 5.95 (1H, d, J 0.8 Hz), 6.90 (1H, s), 7.01 (2H, s), 7.11 (1H, d, J 9.2 Hz), 7.23 (2H, dd, J 13.7, 6.2 Hz), 7.35 (2H, m), 7.48 (2H, d, J 7.4 Hz).

EXAMPLE 10

(3R,5R,6S)-6-Phenyl-3-(2-(pyrid-2-yl)-5-(trifluoromethoxy)phenyl)-7-aza-1-oxa-spiro[4.5]decane The compound of Description 26 was deprotected according to the method illustrated in Example 9 to afford the title compound as the dihydrochloride salt. free base: $^1$H NMR (CDCl$_3$, 360 MHz), δ 1.36 (3H, m), 2.08 (3H, m), 2.32 (1H, qn, J 8.3 Hz), 2.70 (1H, td, J 10.0, 2.6 Hz), 3.19 (1H, m), 3.53 (1H, s), 3.58 (1H, dd, J 10.3, 8.5), 3.92 (1H, t, J 7.9 Hz), 6.93 (1H, d, J 7.8 Hz), 7.18 (4H, m), 7.88 (5H, m), 7.60 (1H, td, J 7.7, 1.8 Hz), 8.47 (1H, s). dihydrochloride salt: MS (ES$^+$) m/z 455 (M+H, 100%). $^1$H NMR (360 MHz, d$_6$-DMSO,) δ 1.82 (3H, m), 2.01 (2H, m), 2.13 (1H, dd, J 9.1, 8.2 Hz), 2.19 (1H, D, J 10.5 Hz), 3.02 (1H, m), 3.19 (1H, D, J 9.8 Hz), 3.8, (2H, m), 4.23 (1H, d, J 10.9 Hz), 7.19 (3H, M), 7.30 (3H, m), 7.59 (2H, m), 7.98 (1h, t, J 6.1 Hz), 8.54 (1H, d, J 4.9 Hz), 8.70 (1H, m), 9.43 (1H, d, J 8.2 Hz).

EXAMPLE 11

(3R,5R,6S)-6-Phenyl-3-(2-pyrid-3-yl)-5-(trifluoromethoxy)phenyl)-7-aza-1-oxa-spiro[4.5]decane This compound was prepared from the compound of Description 27 according to the method illustrated in Example 9 to afford the dihydrochloride salt. MS (ES$^+$) m/z 455 (M$^+$+1, 100%) $^1$H NMR (360 MHz, CDCl$_3$) δ 1.52–1.76 (3H, m), 2.0–2.2 (5H, m), 2.73 (1H, t, J 12 Hz), 3.16–3.19 (1H, m), 3.41 (1H, s), 3.58 (1H, t, J 9.0 Hz), 1H, t, J 8.0 Hz), 7.02–7.26 (10H, m), 8.19 (1H, d, J 2.0 Hz), 8.62 (1H, dd, J 2.0, 2 Hz).

EXAMPLE 12

(3R,5R,6S)-6-phenyl-3-(2-(pyrid-4-yl)-5-(trifluoromethoxy)phenyl-7-aza-1-oxa-spiro[4.5]decane This compound was prepared from the compound of Description 28 according to the method illustrated in Example 9 to afford the dihydrochloride salt. Anal. Calcd. for C$_{26}$H$_{25}$F$_3$N$_2$O$_2$.2HCl.H$_2$O: C, 57.25; H, 5.36; N, 5.13. Found: C, 57.48; H, 4.96; N, 5.28. MS (ES$^+$) m/z 455 (M$^+$+1, 100%)

EXAMPLE 13

(3R,5R,6S)-6-phenyl-3-(2-oxazol-2-yl)-5-(trifluoromethoxy)phenyl)-7-aza-1-oxa-spiro[4.5]decane This compound was prepared from the compound of Description 29 according to the method illustrated in Example 9 to afford the hydrochloride salt. MS (ES) m/z 445 (M$^+$1, 100%). $^1$H NMR (250 MHz, CDCl$_3$) δ 1.59–1.70 (3H, m). 2.01–2.17 (1H, m), 2.27 (1H, dd, J 13.0, 8.3 Hz), 2.76 (1H, t, J 10.0 Hz), 3.12–3.27 (2H, m), 3.48 (1H, s), 3.64 (1H, t, J 9.0 Hz), 4.05 (1H, t, J 7.7 Hz), 7.07–7.17 (1H, m), 7.20 (1H, brs), 7.26–7.33 (4H, m), 7.48–7.52 (2H, m), 7.57 (1H,s), 7.75 (1H, d, 8.5 Hz).

EXAMPLE 14

(3R,5R,6S)-6-phenyl-3-(2-pyrazin-2-yl)-5-(trifluoromethoxy)phenyl)-7-aza-1-oxa-spiro[4.5]decane This compound was prepared from the compound of Description 30 according to the method illustrated in Example 9 to afford the hydrochloride salt. MS (ES) m/z 456 (M$^+$+1, 100%). $^1$H NMR (250 MHz, CDCl$_3$) δ 1.59–1.82 (3H, m), 2.04–2.24 (3H, m), 2.28–2.48 (1H, m), 2.72–2.82 (1H, m), 3.24–3.36 (1H, m), 3.61 (1H, t, J 9.3 Hz), 3.76 (1H, s), 3.94–4.08 (1H,m), 7.07–7.44 (8H, m), 8.30 (1H, s), 8.45 (1H, s), 8.58 (1H, s), 9.06 (1H, br), 10.08 (1H, br).

EXAMPLE 15

(3R,5R,6S)-6-phenyl-3-(2-pyrimidin-2-yl)-5-(trifluoromethoxy)phenyl)-7-aza-1-oxa-spiro[4.5]decane This compound was prepared from the compound of Description 31 according to the method illustrated in Example 9 to afford the hydrochloride salt. MS (ES) m/z 456 (M$^+$+1, 100%). $^1$H NMR (360 MHz, CDCl$_3$) δ 1.57–1.74 (3H, m), 1.80–1.91 (1H, m), 2.00–2.18 (3H, m), 2.70 (1H, t, J 12.0 Hz), 3.19 (1H, d, J 10.4 Hz), 3.48 (1H, s), 3.62 (1H, dd, J 9.7, 8.6 Hz), 3.88 (1H, t, J 8.0 Hz), 4.13 (1H, br, NH), 7.02 (1H, d, J 8.6 Hz), 7.05–7.16 (5H, m), 7.22–7.28 (2H, m), 8.30 (2H, s), 9.25 (1H, s).

EXAMPLE 16

(3R,5R,6S)-3-(2-(Fur-2-yl)-5-(trifluoromethoxy)phenyl)-6-phenyl-7-aza-1-oxa-spiro[4.5]decane This compound was prepared from the compound of Description 32 according to the method illustrated in Example 9 to afford the hydrochloride salt. MS (ES) m/z 444 (M$^+$+1, 100%). $^1$H NMR (250 MHz, CDCl$_3$) δ 1.64–1.78 (3H, m), 2.07 (1H, d, J 14.5 Hz), 2.19 (1H, dd, J 13.0, 8.5 Hz), 2.36–2.58 (1H, m), 2.60–2.82 (2H, m), 3.32–3.38 (1H, m), 3.62 (1H, t, J 9.3 Hz), 3.84 (1H, d, J 10.3 Hz), 4.02 (1H, t, J 8 Hz), 5.85 (1H, d, J 3.3 Hz), 6.33 (1H, dd, J 3.3, 1.8 Hz), 6.96–7.04 (2H, m), 7.22–7.39 (5H, m), 7.52–7.58 (2H, m).

EXAMPLE 17

*(3R,5R,6S)-3-(2-Fur-2-yl)-5-(trifluoromethoxy)phenyl)-6-phenyl-7-(1,2,4-triazol-3-ylmethyl)-aza-1-oxa-spiro[4.5]decane The amine of Example 16 (100 mg) was dissolved in dimethylformamide (0.7 ml) and treated with N-formyl-2-chloroacetimidrazone (32 mg) and heated at 60° C. for 3 hours before diluting with xylene (10 ml) and heating at 140° C. for a further 4 hours. The mixture was then filtered through celite washing with ethyl acetate. Evaporation yielded an off white solid which was purified by chromatography on silica(eluting with 10% methanol in dichloromethane) to give a white solid which was crystalized from ether/ethyl acetate to yield the title compound as white crystals.(90 mg, 77%). MS (ES) m/z 525 (M$^+$+1, 100%). $^1$H NMR (360 MHz, CDCl$_3$) d 2.08–2.30 (6H, m), 2.32–2.36 (1H, m), 2.54–2.68 (1H, m), 2.96–3.06 (1H,m) 3.26 (1H, s), 3.35 (1H, d, J=15.5 Hz), 3.61 (1H, dd, J=10.4, 8.6 Hz), 3.69 (1H, d, J=15.5 Hz), 3.97 (1H, t, J=8 Hz), 5.84 (1H, d, J=3.2 Hz), 6.35 (1H, dd, J=3.3, 1.8 Hz), 7.03–7.08 (2H, m), 7.24–7.41 (5H, m), 7.43–7.49 (2H, m), 7.88 (1H, s).

EXAMPLE 18

(3R,5R,6S)-3-(2-(Oxazol-5-yl)-5-(trifluoromethoxy)phenyl)-6-phenyl-1-oxa-7-aza-spiro[4.5]decane This compound was prepared from the compound of Description 35 according to the method illustrated in Example 9 to afford the hydrochloride salt. $^1$H NMR (CDCl$_3$, 360 MHz), δ 1.65 (4H, m), 2.04 (1H, d), 2.21 (1H, dd, J=12.9, 8.3 Hz), 2.52 (1H, qn), 2.79 (1H, t, J=12.3 Hz), 3.20 (1H, d), 3.54 (1H, s), 3.63 (1H, dd, J=10.1 8.7 Hz), 3.98 (1H, t, J=8.0 Hz), 6.59 (1H, s). 7.07 (1H, d, J=8.6 Hz), 7.15 (1H, s), 7.30 (3H, m), 7.38 (1H, d, J=8.6 Hz). 7.43 (2H, m), 7.76 (1H, s). M/Z (ES+) 445 (M+H, 100%).

EXAMPLE 19
(3R,5R,6S)-3-(2-(5-Methylfur-2-yl)-5-(trifluoromethoxy) phenyl)-6-phenyl-7-aza-1-oxa-spiro[4.5]decane This compound was prepared from the compound of Description 36 according to the method illustrated in Example 9 to afford the hydrochloride salt. MS (ES) m/z 458 (M$^+$+1, 100%). $^1$H NMR (360 MHz, CDCl$_3$) d 1.66–1.75 (3H, m), 2.04–2.10 (1H, m), 2.21 (1H, dd, J=13.0 8.6 Hz), 2.29 (3H, s), 2.39–2.44 (1H, m), 2.68–2.80 (2H, m), 3.31–3.36 (1H, m), 3.64 (1H, t, J=9.4 Hz), 3.86 (1H, d, J=11.2 Hz), 4.02 (1H, t, J=8.3 Hz), 5.60 (1H, d, J=2.9 Hz), 5.90 (1H, s), 7.02–7.04 (2H, m), 7.26–7.42 (4H, m), 7.58–7.60 (2H, m).

EXAMPLE 20
(3R,5R,6S)-3-(2-(5-Methylisoxazol-4-yl)-5-(trifluoromethoxy)phenyl)-6-phenyl-7-aza-1-oxa-spiro[4.5]decane This compound was prepared from the compound of Description 37 according to the method illustrated in Example 9 to afford the hydrochloride salt. MS (ES) m/z 456 (M$^+$+1, 100%). $^1$H NMR (360 MHz, CDCl$_3$) d 163–1.71 (3H, m), 1.87(3H,s), 2.02–2.06 (1H, m), 2.38–2.48 (1H, m), 2.76–2.84 (2H, m), 3.33–3.38 (1H, m), 3.54 (1H, dd, J=10.4 9.0 Hz), 3.77 (1H, d, J=10.8 Hz). 3.88 (1H, t, J=7.9 Hz), 6.98 (1H, d, J=9.4 Hz), 7.04–7.05 (2H, m), 7.16–7.21 (2H, m), 7.37–7.41 (3H, m), 7.78 (1H, s).

EXAMPLE 21
(3R,5R,6S)-3-(Thiophen-2-yl-5-(trifluoromethoxy)phenyl)-6-phenyl-1-oxa-7-aza-spiro[4.5]decane This compound was prepared from the compound of Description 37 according to the method illustrated in Example 9 to afford the hydrochloride salt. MS (ES) m/z 460 (M+H, 100%). $^1$H NMR (D$_2$O, 360 MHz), δ 1.44 (1H, t), 1.74–2.04 (6H, m), 3.01 (1H, t), 3.16 (1H, t, J=9.2 Hz), 3.34 (1H, d), 3.52 (1H, t), 3.99 (1H, s), 6.01 (1H, d, J=4.9 Hz), 6.13 (1H, s), 6.45 (1H, d, J=8.4 Hz), 6.51 (1H, d), 6.86 (1H, s), 7.08 (1H, m), 7.18 (5H, m).

We claim:
1. A compound of the formula (I):

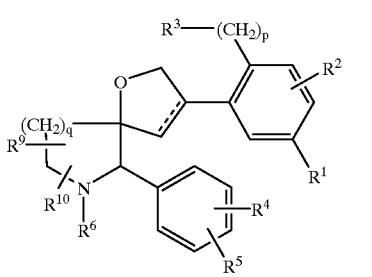

wherein
- $R^1$ represents hydrogen, hydroxy, $C_{1-6}$alkyl, $C_{2-6}$alkenyl, $C_{3-7}$cycloalkyl, $C_{3-7}$cycloalkyl$C_{1-4}$alkyl, fluoro$C_{1-6}$alkyl, $C_{1-6}$alkoxy, fluoro$C_{1-6}$alkoxy, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloaklyl$C_{1-4}$alkoxy, phenoxy, benzyloxy, cyano, halogen, NR$^{11}$COR$^{14}$, NR$^a$R$^b$, SR$^a$, SOR$^a$, SO$_2$R$^a$, OSO$_2$R$^a$, or $C_{1-4}$alkyl substituted by cyano or CO$_2$R$^a$, R$^a$ and R$^b$ each independently represent hydrogen, $C_{1-4}$alkyl or fluoro$C_{1-4}$alkyl;
- $R^2$ represents hydrogen, halogen, $C_{1-6}$alkyl or $C_{1-6}$alkoxy; or when $R^2$ is adjacent to $R^1$, they may be joined together such that there is formed a 5- or 6-membered saturated or unsaturated ring containing one or two oxygen atoms;
- $R^3$ represents a 5- or 6-membered aromatic heterocyclic group containing 1, 2, 3 or 4 heteroatoms, selected from nitrogen, oxygen and sulphur, which group is optionally substituted by one or two groups selected from halogen, $C_{1-6}$alkyl, $C_{1-6}$alkoxy, $C_{3-7}$cycloalkyl, $C_{3-7}$cycloalkyl$C_{1-4}$alkyl, trifluoromethyl, trifluoromethoxy, nitro, cyano, SR$^a$, SOR$^a$, SO$_2$R$^a$, COR$^a$, CO$_2$R$^a$, phenyl, —(CH$_2$)$_r$NR$^a$R$^b$, —(CH$_2$)$_r$NR$^a$COR$^b$, —(CH$_2$)$_r$CONR$^a$R$^b$, or CH$_2$C(O)R$^a$, where R$^a$ and R$^b$ are each independently hydrogen or $C_{1-4}$alkyl and r is zero, 1 or 2;
- $R^4$ represents hydrogen, halogen, $C_{1-6}$alkyl, $C_{1-6}$alkoxy, trifluoromethyl, trifluoromethoxy, nitro, cyano, SR$^a$, SOR$^a$, SO$_2$R$^a$, CO$_2$R$^a$, CONR$^a$R$^b$, $C_{2-6}$alkenyl, $C_{2-6}$alkynyl or $C_{1-4}$alkyl substituted by $C_{1-4}$alkoxy, where R$^a$ and R$^b$ each independently represent hydrogen or $C_{1-4}$alkyl;
- $R^5$ represents hydrogen, halogen, $C_{1-6}$alkyl, trifluoromethyl or $C_{1-6}$alkoxy substituted by $C_{1-4}$alkoxy;
- $R^6$ represents hydrogen, COR$^a$, CO$_2$R$^a$, COCONR$^a$R$^b$, COCO$_2$R$^a$, $C_{1-6}$alkyl optionally substituted by a group selected from (CO$_2$R$^a$, CONR$^a$R$^b$, hydroxy, cyano, COR$^a$, NR$^a$R$^b$, C(NOH)NR$^a$R$^b$, CONHphenyl($C_{1-4}$ alkyl), COCO$_2$R$^a$, CONHNR$^a$R$^b$, C(S)NR$^a$R$^b$, CONR$^a$C$_{1-6}$alkylR$^{12}$, CONR$^{13}$C$_{2-6}$alkenyl, CONR$^{13}$C$_{2-6}$alkynyl, COCONR$^a$R$^b$, CONR$^a$C(NR$^b$) NR$^a$R$^b$, CONR$^a$heteroaryl, and phenyl optionally substituted by one, two or three substituents selected from $C_{1-6}$alkyl, $C_{1-6}$alkoxy, halogen and trifluoromethyl), where R$^a$ and R$^b$ are each independently hydrogen or $C_{1-4}$alkyl;
- or $R^6$ represents a group of the formula —CH$_2$C≡CCH$_2$NR$^7$R$^8$ where R$^7$ and R$^8$ are as defined below;
- or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula ZNR$^7$R$^8$ where Z is $C_{1-6}$alkylene or $C_{3-6}$cycloalkyl;
- $R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;
- $R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;
- or R$^7$, R$^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is $C_{1-4}$alkyl optionally substituted by hydroxy or $C_{1-4}$alkoxy;
- or R$^7$, R$^8$ and the nitrogen atom to which they are attached form a non-aromatic azabicyclic ring system of 6 to 12 ring atoms;
- or Z, R$^7$ and the nitrogen atom to which they are attached form a heteroaliphatic ring to 4 to 7 ring atoms which may optionally contain an oxygen ring atom;
- R$^9$ and R$^{10}$ each independently represent hydrogen, halogen, $C_{1-6}$alkyl, CH$_2$OR$^d$, oxo, CO$_2$R$^a$ or CON- R$^a$R$^b$ where R$^a$ and R$^b$ are each independently hydrogen or C$_{1-6}$alkyl and R$^d$ represents hydrogen, C$_{1-6}$alkyl or phenyl;

R$^{11}$ represents hydrogen, C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy or hydroxyl;

R$^{12}$ represents OR$^a$, CONR$^a$R$^b$ or heteroaryl, where R$^a$ and R$^b$ are each independently hydrogen or C$_{1-4}$alkyl;

R$^{13}$ represents H or C$_{1-6}$alkyl;

R$^{14}$ represents C$_{1-6}$alkyl, C$_{1-6}$alkoxy, fluoroC$_{1-6}$alkyl or phenyl;

p is zero or 1;

q is 1 or 2; and the broken line represents a double bond;

or a pharmaceutically acceptable salt thereof.

2. The compound of claim 1 of the formula (Ia) or a pharmaceutically acceptable salt thereof:

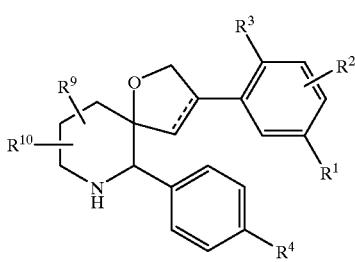

(Ia)

wherein R$^1$, R$^2$, R$^3$, R$^4$, R$^9$, R$^{10}$ and the broken line are as defined in claim 1.

3. The compound as claimed in claim 1 wherein R$^1$ is a methyl, trifluoromethyl, methoxy, ethoxy, isopropoxy or trifluoromethoxy group.

4. The compound as claimed in claim 1 wherein R$^2$ is a hydrogen, fluorine or chlorine atom.

5. The compound as claimed in claim 1 wherein R$^3$ is a group selected from furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each heteroaryl group being optionally substituted as defined in claim 1.

6. The compound as claimed in claim 5 wherein R$^3$ is the group

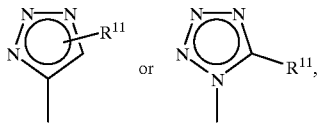

where R$^{11}$ is hydrogen, halogen, C$_{1-6}$alkyl, C$_{1-6}$alkoxy, CF$_3$, OCF$_3$, NO$_2$, CN, SR$^a$, SOR$^a$, SO$_2$R$^a$, COR$^a$, CO$_2$R$^a$, (CH$_2$)$_r$CONR$^a$R$^b$, (CH$_2$)$_r$NR$^a$R$^b$ or (CH$_2$)$_r$NR$^a$COR$^b$, where R$^a$ and R$^b$ are hydrogen or C$_{1-4}$alkyl, and r is zero, 1 or 2.

7. The compound as claimed in claim 1 wherein R$^4$ is a hydrogen atom or a fluorine atom.

8. The compound as claimed in claim 1 wherein R$^5$ is a hydrogen atom.

9. The compound as claimed in claim 1 wherein R$^6$ is a hydrogen atom or a C$_{1-6}$alkyl group substituted by a 5-membered heterocyclic ring containing 2 or 3 nitrogen atoms as defined in claim 1.

10. The compound as claimed in claim 1 wherein R$^9$ and R$^{10}$ are both hydrogen atoms.

11. The compound as claimed in claim 1 wherein p is zero.

12. The compound as claimed in claim 1 wherein q is 2.

13. The compound as claimed in claim 1 wherein the double bond represented by the broken line is absent.

14. A compound which is selected from:

(6S,5R)-3-(5-methoxy-2-(5-trifluoromethyl)tetrazol-1-yl)phenyl)-6-phenyl-1-oxa-7-aza-spiro[4.5]dec-3-ene;

(6S,5R,3S)-3-(5-methoxy-(2-(5-trifluoromethyl)tetrazol-1-yl)phenyl)-6-phenyl-1-oxa-7-aza-spiro[4.5]decane;

(6S,5R)-3-(5-methoxy-2-(tetrazol-1-yl)phenyl)-6-phenyl-1-oxa-7-aza-spiro[4.5]dec-3-ene;

(6S,5R,3S)-3-(5-methoxy-2-(tetrazol-1-yl)phenyl)-6-phenyl-1-oxa-7-aza-spiro[4.5]decane;

(5R,6S)-3-(2-(fur-2-yl)-5-(trifluoromethoxy)phenyl)-6-phenyl-7-aza-1-oxa-spiro[4.5]dec-3-ene;

(3S,5R,6S)-3-(2-fur-2-yl)-5-(trifluoromethoxy)phenyl)-6-phenyl-7-aza-1-oxa-spiro[4.5]decane;

(3S,5R,6S)-6-phenyl-3-(2-(thiazol-2-yl)-5-(trifluoromethoxy)phenyl)-7-aza-1-oxa-spiro[4.5]decane;

(3S,5R,6S)-6-phenyl-3-(2-(thien-2-yl)-5-(trifluoromethoxy)phenyl)-7-aza-1-oxa-spiro[4.5]decane;

(3R,5R,6S)-3-(2-(fur-3-yl)-5-(trifluoromethoxy)phenyl)-6-phenyl-7-aza-1-oxa-spiro[4.5]decane;

(3R,5R,6S)-6-phenyl-3-(2-(pyrid-2-yl)-5-(trifluoromethoxy)phenyl)-7-aza-1-oxa-spiro[4.5]decane;

(3R,5R,6S)-6-phenyl-3-(2-(pyrid-3-yl)-5-(trifluoromethoxy)phenyl)-7-aza-1-oxa-spiro[4.5]decane;

(3R,5R,6S)-6-phenyl-3-(2-(pyrid-4-yl)-5-(trifluoromethoxy)phenyl)-7-aza-1-oxa-spiro[4.5]decane;

(3R,5R,6S)-6-phenyl-3-(2-(oxazol-2-yl)-5-(trifluoromethoxy)phenyl)-7-aza-1-oxa-spiro[4.5]decane;

(3R,5R,6S)-6-phenyl-3-(2-(pyrazin-2-yl)-5-(trifluoromethoxy)phenyl)-7-aza-1-oxa-spiro[4.5]decane;

(3R,5R,6S)-6-phenyl-3-(2-(pyrimidin-2-yl)-5-(trifluoromethoxy)phenyl)-7-aza-1-oxa-spiro[4.5]decane;

(3R,5R,6S)-3-(2-(fur-2-yl)-5-(trifluoromethoxy)phenyl)-6-phenyl-7-aza-1-oxa-spiro[4.5]decane;

(3R,5R,6S)-3-(2-(fur-2-yl)-5-(trifluoromethoxy)phenyl)-6-phenyl-7-(1,2,4-triazol-3-ylmethyl)-aza-1-oxa-spiro[4.5]decane;

(3R,5R,6S)-3-(oxazol-3-yl-5-(trifluoromethoxy)phenyl)-6-phenyl-1-oxa-7-aza-spiro[4.5]decane;

(3R,5R,6S)-3-(2-(5-methylfur-2-yl)-5-(trifluoromethoxy)phenyl)-6-phenyl-7-aza-1-oxa-spiro[4.5]decane;

(3R,5R,6S)-3-(2-(5-methylisoxazol-4-yl)-5-(trifluoromethoxy)phenyl)-6-phenyl-7-aza-1-oxa-spiro[4.5]decane;

(3R,5R,6S)-3-(thiophen)-2-yl-5-(trifluoromethoxy)phenyl)-6-phenyl-1-oxa-7-aza-spiro[4.5]decane;

or a pharmaceutically acceptable salt thereof.

15. The compound as claimed in claim 1 which has the sterochemistry shown in formula (Ic)

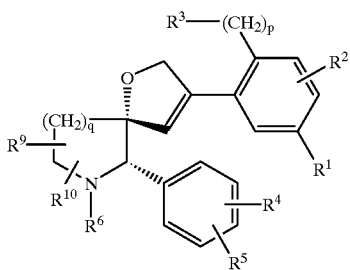
(Ic)

wherein $R^1$, $R^2$, $R^3$, $R^4$, $R^5$, $R^6$, $R^9$, $R^{10}$, p, q and the broken line are as defined in claim 1.

16. The compound as claimed in claim 15 wherein the double bond represented by the broken line is absent and the stereochemistry of the 3-position is 3—(R).

17. A pharmaceutical composition comprising a compound as claimed in claim 1 in association with a pharmaceutically acceptable carrier or excipient.

18. A method for the treatment of physiological disorders associated with an excess of tachykinins, which method comprises administration to a patient in need thereof of a tachykinin reducing amount of a compound according to claim 1.

19. A method according to claim 18 for the treatment of pain or inflammation, migraine, emesis or postherpetic neuralgia.

20. A process for the preparation of a compound as claimed in claim 1 which comprises:

(A.1), where the broken line is absent, reducing a compound of formula (IIA)

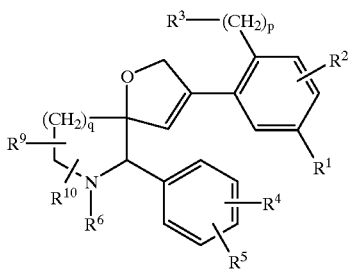
(IIA)

wherein $R^1$, $R^2$, $R^3$, $R^4$, $R^5$, $R^6$, $R^9$, $R^{10}$, p and q are as defined in claim 1;

(A.2), where the broken line is absent, reducing a compound of formula (IIB)

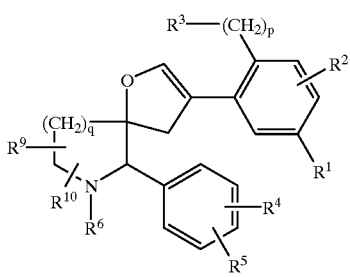
(IIB)

using the reaction conditions described in process (A.1), above; or (B), where the broken line is a double bond, reacting a compound of formula (III)

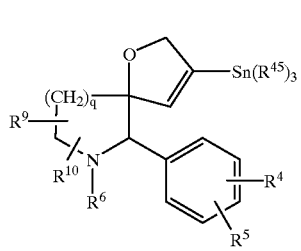
(III)

wherein $R^4$, $R^5$, $R^6$, $R^9$, $R^{10}$ and q are as defined in claim 1 and each $R^{45}$ is a $C_{1-4}$alkyl group, with a compound of formula (IV)

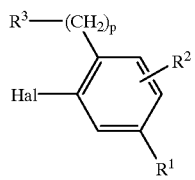
(IV)

wherein $R^1$, $R^2$, $R^3$ and p are as defined in claim 1 and Hal is a halogen atom; or (C) reacting a compound of formula (V)

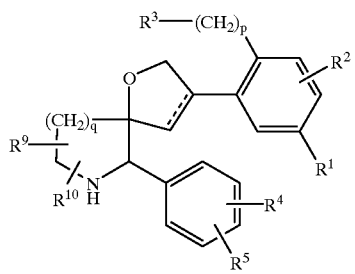
(V)

wherein $R^1$, $R^2$, $R^3$, $R^4$, $R^5$, $R^9$, $R^{10}$, p, q and the broken line are as defined in claim 1 with a compound of formula (VI):

LG—$R^{6a}$  (VI)

where $R^{6a}$ is a group of the formula $R^6$ as defined in claim 1 (other than H) or a precursor therefor and LG is a leaving group; and, if $R^{6a}$ is a precursor group, converting it to a group $R^6$; or (D) interconversion of a compound of formula (I) to give another compound of formula (I); or (E), where p is zero and $R^3$ is a tetrazol-1-yl group, reacting an of intermediate of formula (VII)

(VII)

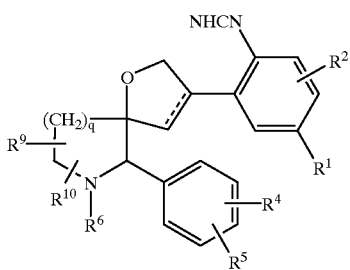

with ammonium chloride and sodium azide; or
(F) a coupling reaction between a compound of formula (VIII) and (IX)

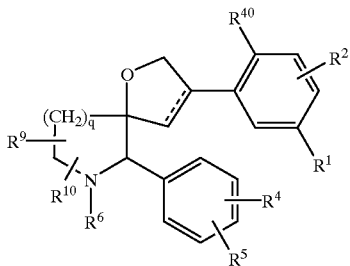
(VIII)

(IX)

wherein one of $R^{40}$ and $R^{41}$ is $B(OH)_2$ or $Sn(alkyl)_3$ or a derivative thereof, and the other is a leaving group; or
(G) cyclising a compound of formula (X)

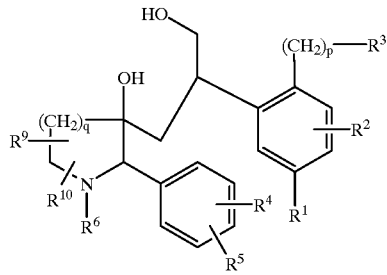
(X)

wherein Y" is —CH$_2$— or —CH$_2$CH$_2$—; or (H), wherein X is —CH$_2$— and Y is —CH$_2$— or —CH$_2$CH$_2$—, reacting a compound of formula (XX)

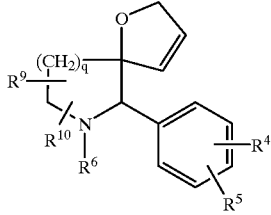
(XX)

with a compound of formula (IV) wherein Hal in formula (IV) is chlorine, bromine or iodine, under the conditions of a reductive Heck reaction; or (J), where the dotted line is a double bond, dehydrating a compound of formula (XXI)

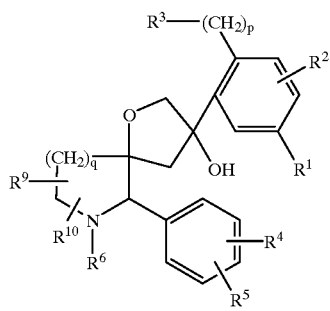
(XXI)

each process being followed, whereby necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

* * * * *